US006923811B1

(12) United States Patent
Carl et al.

(10) Patent No.: US 6,923,811 B1
(45) Date of Patent: Aug. 2, 2005

(54) SYSTEMS AND METHODS FOR SPINAL FIXATION

(75) Inventors: Allen Carl, Slingerlands, NY (US); Ricky D. Hart, Plainville, MA (US); Josef K. Winkler, Reading, PA (US)

(73) Assignee: Spray Venture Partners, Newton, MA (US)

( * ) Notice: Subject to any disclaimer, the term of this patent is extended or adjusted under 35 U.S.C. 154(b) by 0 days.

(21) Appl. No.: 10/019,265

(22) PCT Filed: May 10, 2000

(86) PCT No.: PCT/US00/12773

§ 371 (c)(1),
(2), (4) Date: Nov. 13, 2001

(87) PCT Pub. No.: WO00/67651

PCT Pub. Date: Nov. 16, 2000

Related U.S. Application Data

(60) Provisional application No. 60/133,356, filed on May 10, 1999.

(51) Int. Cl.[7] .............................................. A61B 17/70
(52) U.S. Cl. ..................................... 606/61; 623/17.11
(58) Field of Search ............................. 606/60, 61, 72, 606/74, 75, 167, 170, 180, 185; 623/17.11–17.16

(56) References Cited

U.S. PATENT DOCUMENTS

| 4,135,506 A | * | 1/1979 | Ulrich .......................... 606/61 |
| 4,790,303 A | * | 12/1988 | Steffee ......................... 606/61 |
| 5,591,235 A | * | 1/1997 | Kuslich ........................ 606/61 |
| 6,190,401 B1 | * | 2/2001 | Green et al. ................. 606/224 |

* cited by examiner

Primary Examiner—Todd E. Manahan
Assistant Examiner—Michael B. Priddy
(74) Attorney, Agent, or Firm—Peter F. Corless; William J. Daley, Jr.; Edwards & Angell, LLP

(57) ABSTRACT

Featured are a method and apparatus for fixing adjacent vertebrate of a spine that avoids the need and associated problems with prior cage or straight rod and screw systems. Methods and apparatus of the invention utilize a new implant member, which preferably is arcuate. Preferred methods of the invention for stabilizing adjacent vertebrae of the spine, include steps of providing a positioning apparatus including two guide sleeves, each guide sleeve having a long axis and locating the two guide sleeves with respect to the adjacent vertebrae such that a vertex formed by the long axis of each guide sleeve is located in the intervertebral space for the adjacent vertebrae. The method further includes forming an aperture in each of the adjacent vertebrae using the guide sleeves and inserting an implant into the apertures formed in each of the adjacent vertebrae so that the implant extends between the adjacent vertebrae and through the intervertebral space. In an alternative method a cutting fixture including a pivot arm is secured to the adjacent vertebrae and a cutting device is secured to the pivot arm. The pivot arm and cutting device are configured and arranged so that rotation of the pivot arm about a particularly located pivot point allows the cutting device to form the aperture in each of the adjacent vertebrae. Another alternative method for fixing adjacent vertebrate of a spine includes the step of forming a common channel in and between the adjacent vertebrae and inserting a biscuit implant in the common so as to bridge between the adjacent vertebrae.

75 Claims, 16 Drawing Sheets

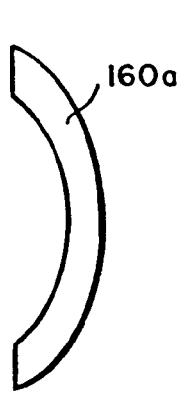
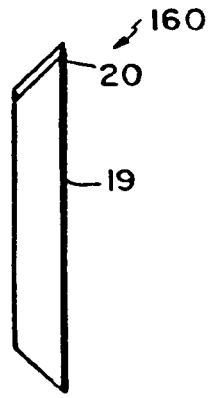
FIG. 7A  FIG. 7B
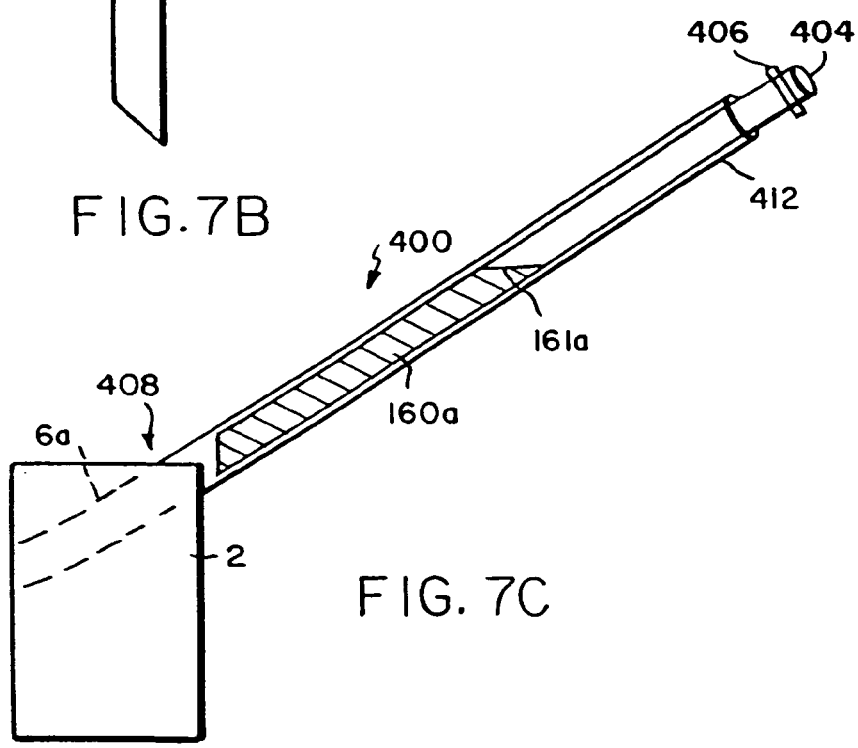
FIG. 7C
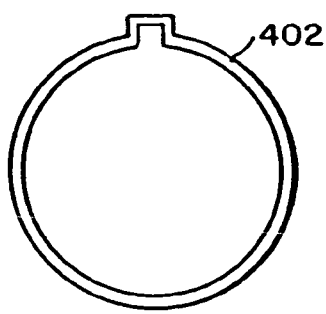
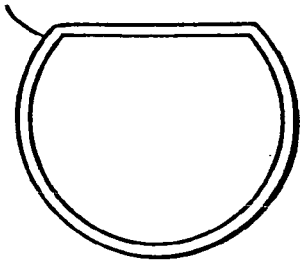
FIG. 8A  FIG. 8B

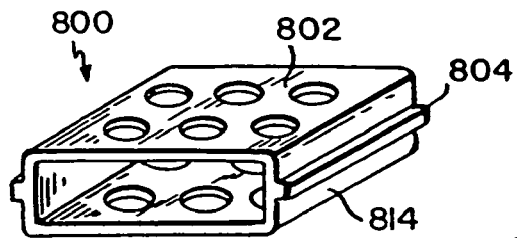
FIG. 13A
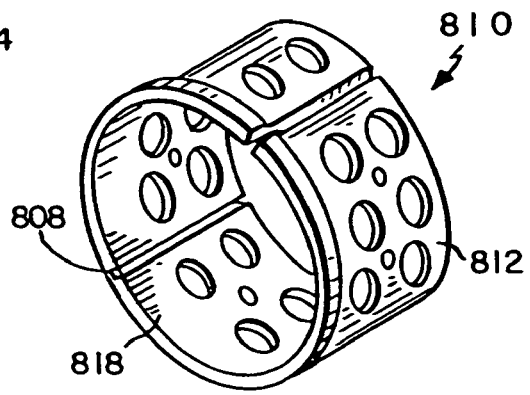
FIG. 13B
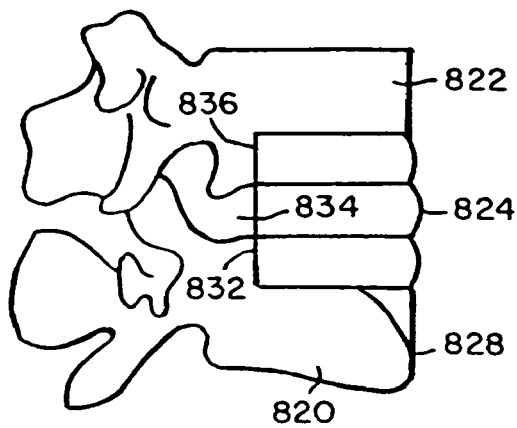
FIG. 13C
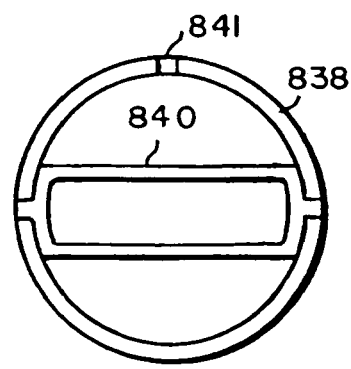
FIG. 13D
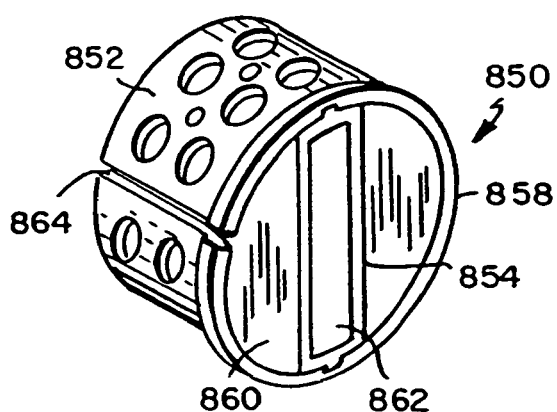
FIG. 13F
FIG. 13E

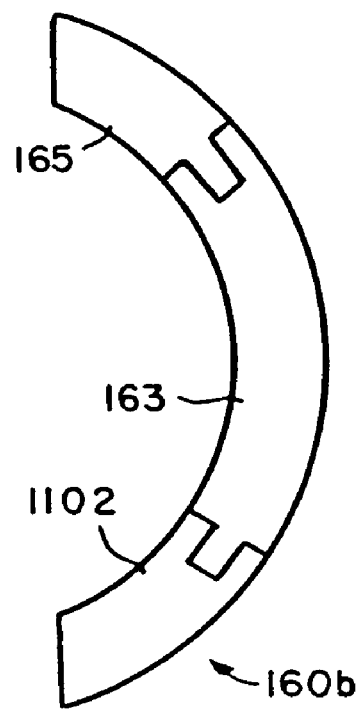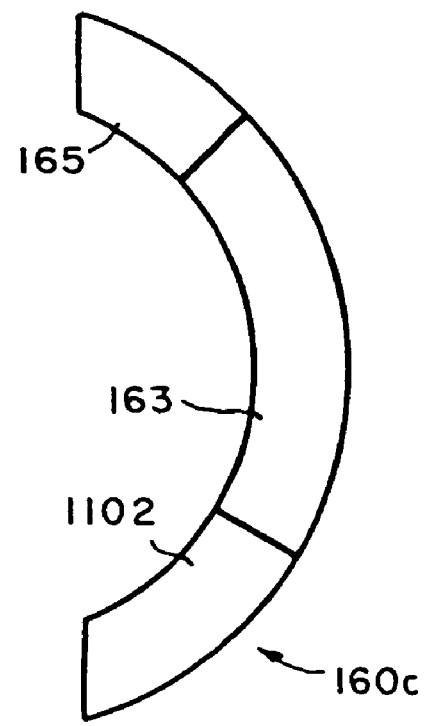
FIG. 17A    FIG. 17B
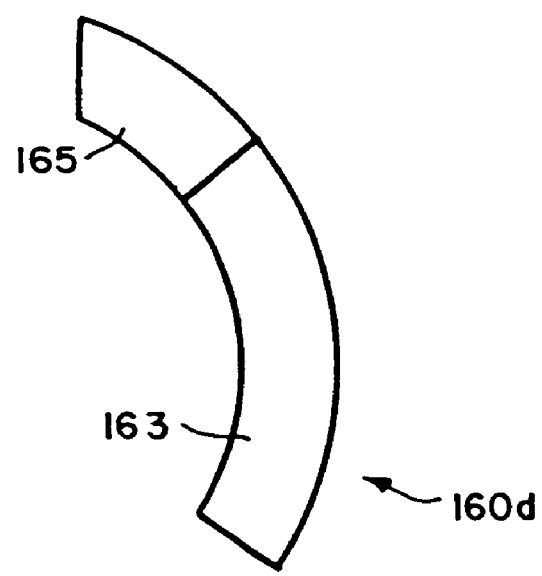
FIG. 17C

SYSTEMS AND METHODS FOR SPINAL FIXATION

This application claims the benefit of U.S. Provisional Application Ser. No. 60/133,356 filed May 10, 1999, and of U.S. application Ser. No. 09/536,732, filed Mar. 28, 2000, which applications are incorporated herein by reference in their emtirety.

BACKGROUND OF THE INVENTION

1. Field of the Invention

The present invention generally relates to methods, systems and apparatuses for bony fixation, more particularly to methods, systems and apparatuses adapted for fixing the bones of the spine, and to methods, systems and apparatuses adapted for securing a prosthetic device within the bones of the human body, more specifically securing a prosthetic device within the bones of the spine.

2. Background of the Invention

Fixation or fusion of vertebral columns with bone or material, rods or plates is a common, long practiced surgical method for treating a variety of conditions. Many of the existing procedures involve the use of components that protrude outwardly, which may contact and damage a body part, such as the aorta, the vena cava, the sympathetic nerves, the lungs, the esophagus, the intestine and the ureter. Also, many constructions involve components that may loosen and cause undesirable problems, often necessitating further surgical intervention. Additionally, limiting the success of these procedures are the bio-mechanical features of the spine itself, whose structure must simultaneously provide support to regions of the body, protect the vertebral nervous system and permit motion in multiple planes.

As indicated above, spinal surgery for spine fusion generally involves using implants and instrumentation to provide support to the affected area of the spine while allowing the bones thereof to fuse. The technology initially evolved using bone chips around and on top of an area of the spine that had been roughened to simulate a fracture in its consistency. The area, having encountered the bone chips, would then proceed to heal like a fracture, incorporating the bone chips. However, surgical procedures dealing with the spine present notable challenges. For example, bioengineers have been required to identify the various elements of the complex motions that the spine performs, and the components of the complex forces it bears. This complexity has made it difficult to achieve adequate stability and effective healing in surgical procedures directed to the spine.

One surgical technique provided by Cloward, involves cutting a dowel type hole with a saw across or through the moveable intervertebral disc and replacing it with a bone graft that was harvested from the hip bone. This procedure limits motion and mobility and results in a fusion of the adjacent vertebral bodies. However, as a result of the complex motions of the spine, it is often difficult to secure the dowel from displacing. Further, it has become apparent over time, however, that this particular technique does not always yield a secure fusion.

Other techniques have been developed that involve the placement of various hardware elements, including rods and hooks, rods and screws and plates and screws. The dowel technique also has advanced over the past five years or so, with dowels being fabricated from cadaver bone or metals such as titanium or stainless steel. These techniques, whether using hardware, dowels or some combination thereof, have a common goal to enhance stability by diminishing movement, thereby resulting in or enhancing the potential of a fusion of adjacent vertebral bones. For example, in one of these other techniques, the disc is removed and adjacent vertebrae are positioned in a stable position by placing a plate against and traversing them, which plate is secured or anchored to each by means of screws.

In another procedure, cages in the form of two parallel circular or rectangular devices are made out of a material such as titanium or stainless steel and these devices are fenestrated. Bone is packed in the center of the devices that will heal to adjacent bone through each fenestration. In this procedure, the disc space is distracted so all ligamentous structures are taut and the bones are held in their normal maximal position of distraction. Because the cages are implanted in spongy bone, they are more likely to collapse the surrounding bone, thus resulting in loss of distraction and subsequently cage dislodgment.

U.S. Pat. No. 5,591,235 reports a certain spinal fixation device and technique for stabilizing vertebrae. In this technique, a hollow screw is inserted into a hole, preferably a hole saw recess, in each adjoining vertebrae. A channel is cut into the vertebrae, which is lined up with corresponding axial slots in the screw. A rod is inserted into the channel and so as to pass through the axial slots in the screw. The rod is secured to each of the screws by means of a locking cap. The rod also is arranged so as to provide a bridge between the hollow screws in the adjoining vertebrae. Certain disadvantages have been surmised using such a device and technique. For example, it has become apparent that the trough in the vertebral bodies destabilizes some of the cortex of the vertebrae body wall, which is the strongest component.

In addition to fixation or fusion of vertebral columns, the prior art also describes methods or other spinal repair procedures, such as discectomy wherein an artificial disc or prosthetic device is placed within the vertebrae of the spine. For such prior art methods and related devices, there have been short comings such as having difficulty in securing the prostheses within the vertebral space or resulting in significant modification or damage to the load bearing surfaces of the vertebrae in an effort to secure the prosthesis.

Thus, it would be desirable to provide a new apparatus, system and methods for spinal fixation that enhances healing of the bone while providing structural support to the spine. It would be particularly desirable to provide such an apparatus, system and method that would involve the use of open surgical or minimally invasive surgical techniques as well as a technique in which the implant burrows in the bone spine, traverses across the disk space, and ends in an adjacent or neighboring vertebrae or vertebras, providing limited or no protrusions. It also would be desirable to provide such an apparatus, system and method where the implant is retained within the bone without requiring contour-varying external vertebral wall fixation as compared to conventional devices, as such a device would avoid many of the problems associated with conventional devices such as blood vessel injury, erosion into organs, as well as placement near nerves. Additionally, it would be desirable to provide such an apparatus, system and method where the implant is retained within the bone and is utilized to secure an artificial prosthesis for example within the vertebral bodies. Such securing is accomplished with or without the use of the annulus, and without insult to portions of the vertebral surfaces bearing significant loading.

SUMMARY OF THE INVENTION

I have now found new methods and apparatus for fixing adjacent vertebrate of a spine. The methods and apparatus of the invention utilize a new implant member, which preferably is arcuate, and avoids the associated problems with prior cage or straight rod and screw systems. It is within the scope of the present invention for the implant member to have any geometric shape or configuration consistent with the intended use including a straight member.

Preferred methods of the invention for stabilizing adjacent vertebrae of the spine, include the steps of providing a positioning apparatus including two guide sleeves, each guide sleeve having a long axis and locating the two guide sleeves with respect to the adjacent vertebrae such that a vertex formed by the long axis of each guide sleeve is located in the intervertebral space for the adjacent vertebrae. The method further includes forming an aperture in each of the adjacent vertebrae using the guide sleeves and inserting an implant into the apertures formed in each of the adjacent vertebrae so that the implant extends between the adjacent vertebrae and through the intervertebral space.

Preferably, the aperture formed in the vertebrae is arcuate and the implant being inserted also is arcuate. The arcuate aperture in each vertebrate can be suitably formed by drilling or other ablation. More particularly, an initial aperture can be drilled in each of the adjacent vertebrae to create intersecting apertures with convergent paths within the intervertebral space; and the initial aperture then enlarged to receive the implant. That enlarging of the initial aperture can be suitably performed by a variety of procedures, e.g. by using a drill bit, a reamer, an awl, impaction drill, shape memory coring device, or curved coring device, or the like.

The step of forming an aperture also can further include inserting a guide member, after drilling of the initial aperture, into one of the guide sleeves, down through the initial aperture in one adjacent vertebrae, through the intervertebral space and into the initial aperture in the other adjacent vertebrae; and advancing an aperture enlarging device over the guide member so as to enlarge the initial aperture. In this case, the aperture enlarging device is suitably a curved reamer or a curved drill bit, and the curved reamer or the curved drill bit is advanced over the guide member so as to form an arcuate aperture in each of the adjacent vertebrae. It also should be appreciated that multiple vertebral holes can be created using the same methods as disclosed herein. In that manner, multiple arcuate implants can be placed, e.g. if greater mechanical stability is considered desirable.

The positioning apparatus can further include a cross member and an intervertebral spacer, preferably where the guide sleeves are pivotally mounted to the cross member and the intervertebral spacer is spaced from the cross member and interconnected thereto at about a mid point between the pivot points for the guide sleeves. In this case, the stabilizing method can further include locating the intervertebral spacer in the intervertebral space between the adjacent vertebrae; and maintaining alignment of the guide sleeves with respect to the adjacent vertebrae so that a consistent angle is maintained between the guide sleeve and the vertebrae during at least a portion of said forming of the aperture. The intervertebral spacer also can be configured so as to provide protection to the spine during the drilling when disposed in the intervertebral space.

In an alternative embodiment, the positioning system being provided includes a cutter bracket system and a curved drilling sub-system affixed thereto. The cutter bracket system includes a pivot arm whose pivot point is disposed between the adjacent vertebrae opposite the intervertebral space. More particularly, the pivot point is at about the midpoint between the adjacent vertebrae. The curved drilling sub-system is affixed to the pivot arm such that as the pivot arm rotates about the pivot point the curved drill sub-system follows an established cutting path. In a more specific embodiment, the drilling sub-system is affixed proximal or at the distal end of the pivot arm. The positioning apparatus according to the alternative embodiment can further include a mechanism that temporarily secures the cutter bracket system to the adjacent vertebra to be fused and which positions and maintains the pivot point at the desired location. Also, the curved drill subsystem can include a curved cannula, a flexible member running through the curved cannula and a cutting burr secured to an end of the flexible member.

As to the step of forming an aperture using a positioning system according to the alternative embodiment, this step includes rotating the pivot arm in one direction about the pivot point so the curved drilling sub-system forms an aperture in one of the adjacent vertebrae and rotating the pivot arm in another direction about the pivot point so as to form an aperture in the other of the adjacent vertebrae. In a more specific embodiment, the step of forming further includes remounting the curved drilling subsystem to the pivot arm before rotating the pivot arm in the another direction so a cutting element of the curved drilling subsystem is aligned for the direction of movement.

As to inserting the implant, the method step includes successively drawing a portion of the implant through the arcuate aperture in one adjacent vertebrae, through the intervertebral space and into the arcuate aperture of the other adjacent vertebrae. In a specific embodiment, the step of inserting includes securing one end of a guide wire to an end of the implant; passing a free end of the guide wire through the arcuate aperture in one of the adjacent vertebrae, through the intravertebral space and through the arcuate aperture in the other adjacent vertebrae; and pulling on the guide wire free end to thereby successively draw the portion of the implant.

In another embodiment, the step of inserting includes inserting a beginning end of the implant into an entrance opening of one of the adjacent vertebrae; applying a force to the portion of the implant extending from the entrance opening so as to drive the implant beginning end though the arcuate aperture in the aperture of said one of the adjacent vertebrae, through the intervertebral space and into the arcuate aperture in the other of the adjacent vertebrae.

The implant being inserted into the final aperture is made from one or more of a metal (e.g., titanium or stainless steel), bone, morphogenic protein (including a combination of bone and bone morphogenic protein), carbon fiber composite, nitinol or biodegradable materials such as polyactic acid or polyglycolic acids and copolymers and other derviatives thereof, or collagen and collagen coated metal or bone. The implant also may comprise an in situ-formed plug where the aperture acts as a mold for an epoxy or other polymer-based system. Also, the implant can be solid or hollow and arranged with or without ingrowth fenestrations and screw holes for post-insertion securement. The implant also can be configured so the implant includes a first and a second section, where a distal end of each of the first and second sections is configured so as to be capable of being secured together. For such an implant, the method further includes the steps of inserting the first section into the aperture in one of the adjacent vertebrae so that the distal end therefore is disposed in the intervertebral space; inserting the implant second section into the aperture in one of the adjacent vertebrae so that the distal end therefore is disposed in the intervertebral space; and securing the distal ends of the first and second sections together. The implant sections being inserted can be arcuate with a radius substantially the same as the arcuate aperture or substantially straight. In particular embodiments, the distal ends of the implant sections are secured to each other by e.g. a nut, bolt, pin, expansion or press-fit device, or interlocking member on the end of each section. Other stabilization methods also can be employed. For instance, a plate can be applied to the vertrebrae surface with attachments at each end of the tunnel traversed by an implant in accordance with the invention.

Another method of the present invention for stabilizing adjacent vertebrae of the spine includes the step of forming a common channel in and between the adjacent vertebrae and inserting a biscuit implant in the common channel so as to bridge between the adjacent vertebrae. In more specific embodiments, the step of forming includes simultaneously cutting a slot, preferably an arcuate slot, in each of the adjacent vertebrae so as to form the common channel and providing a device configured so as to be capable of simultaneously cutting the slot in each of the adjacent vertebrae. Also for said step of inserting, the biscuit implant can be further configured so as to include a spacer element that is received in the intervertebral space between the adjacent vertebrae when the biscuit is disposed in the common channel.

In another alternative aspect of the invention, a diskectomy can be performed and a stabilizing wedge (inner) implant inserted between the vertebrae. The wedge (inner tool) establishes lordosis, provides a construction reference, and carries on it the stabilizing wedge implant. Retracted stop-cut blades on the inner tool are then engaged, cutting into the vertebrae in the vertical plane. A hole saw can be used to create a circular cut in the vertebrae to facilitate insertion of the outer implant. Once the cut is complete, the bone harvested in the tubular cutter can be manipulated into the implant. A circular (outer) implant is then inserted over the inner tool. The outer tool then references the position of the inner tool and guides the implant into place. After the two implants nest together along a key and groove, the outer tool is removed. A fenestrated circular member then replaces the outer cutting tool and the inner tool is rotated about 90 degrees and then removed. Working together, the two rotated implants capture the vertebral body sections, which are now rotated about 90 degrees and through their many holes, provide blood exchange with the adjacent bone to accomplish fusion.

Also featured is a system and apparatus embodying the described methods or techniques for internal fixation of the spine.

Other aspects and embodiments of the invention are discussed below.

BRIEF DESCRIPTION OF THE DRAWING

FIGS. 7A–C are schematic views of the implantation of a fixating member made from nitinol;

FIGS. 8A–B are exemplary cross sectional views of a guide sleeve including a mechanical guide to guide the nitinol fixating member during insertion;

FIGS. 13A–13F illustrate an alternative implant system of the invention; where FIG. 13A is an isometric view of an inner implant, FIG. 13B is an isometric view of an outer implant, FIG. 13C is a lateral view showing a preferred positioning of the implant system, FIG. 13D is an anterior view of the outer implant within which the inner implant is secured, FIG. 13F is an anterior view of the outer and inner implant after rotation, and FIG. 13F is a perspective view of an embodiment of the implant system;

FIGS. 17A–C are schematic views of exemplary implants useable for securing a prosthetic device.

DETAILED DESCRIPTION OF THE INVENTION

Figure 1A:
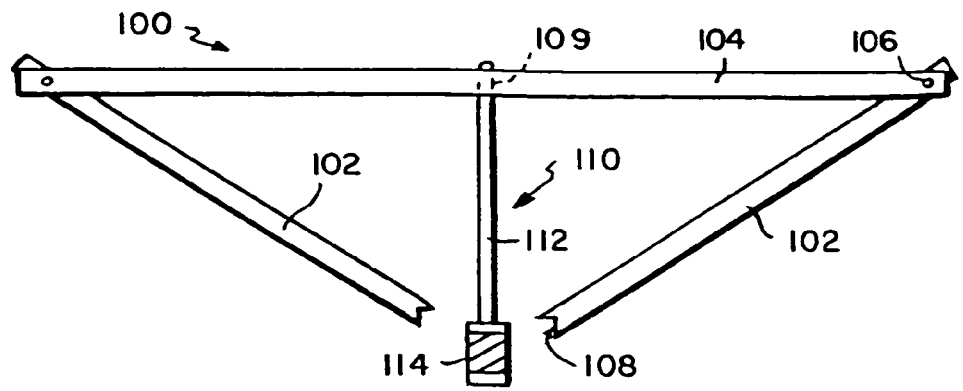
FIG. 1A is a schematic view of a positioning jig according to the present invention.
Figure 1B:
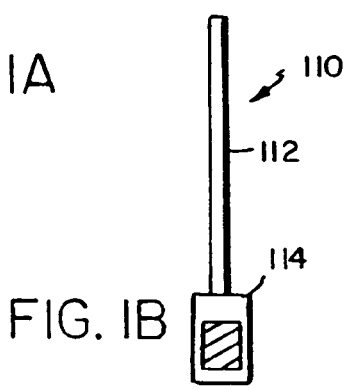
FIG. 1B is a front view of the intervertebral spacing member of FIG. 1A.
Figure 2A:
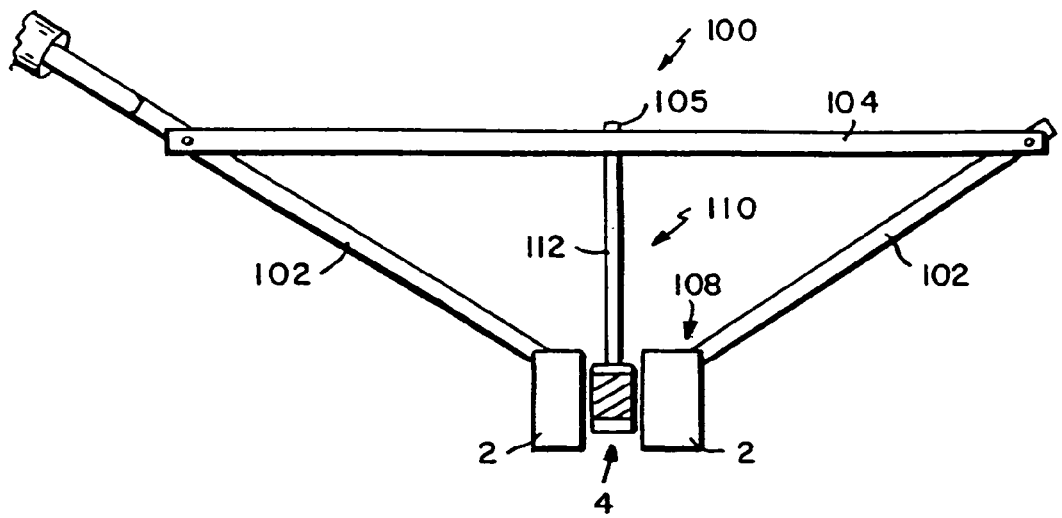
FIG. 2A is a schematic view of the positioning jig of FIG. 1A disposed about two vertebral bodies.

Referring now to the various figures of the drawing wherein like reference characters refer to like parts, there is shown in FIGS. 1–2 various schematic views of a drill guide or positioning jig 100 that positions or aligns the drill bits before making the holes in each of the vertebral bodies 2. The positioning jig 100 includes two guide sleeves 102, a cross member 104 and an intervertebral spacing member 110. Each guide sleeve 102 preferably is a hollow tubular member having a lumen or passage therein for receiving and guiding the means for forming at least the initial aperture in the adjacent vertebrae such as a drill bit 150 (FIG. 3B). As indicated elsewhere herein, the aperture may be formed using other techniques such as the ablation of bone by an energy source, e.g., high-pressure water, high-pressure air, ultrasound, or a laser. As such, it shall be understood that the internal sizing and configuration of the guide sleeves is established to accommodate the particular mechanism used for forming the aperture.

The guide sleeves 102 are mounted to the cross member 104 in such a way that they are each pivotal about the cross member and so each can be secured or locked in a particular angular position with respect to the cross member. Although a single mounting/pivot point 106 is illustrated, it is within the scope of the present invention for the cross member 104 and each guide sleeve 102 to be configured with a plurality or more of such pivot/mounting points. In an exemplary embodiment, the cross member 104 and guide sleeves 102 are constructed from stainless steel; and each guide sleeve is pivotally secured to the cross member by screws.

Figure 3A:
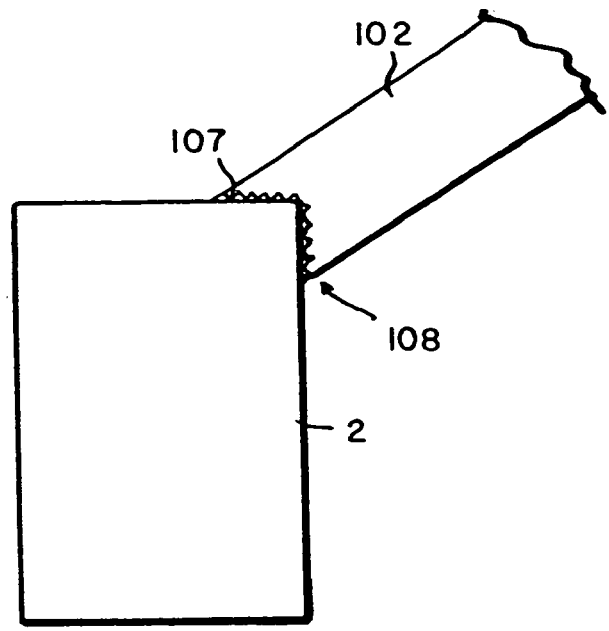
FIGS. 3A–E are schematic views that illustrate the various steps of the process to form a hole in each vertebral body for implanting a fixating member therein.

The distal end 108 of each guide sleeve 102 is configured for mechanically engaging a surface, edge, corner or other surface artifact or feature of the vertebral body 2. In an exemplary embodiment, and as more clearly illustrated in FIG. 3A, the guide sleeve distal end 108 is configured or arranged with a cutout that is designed to accept the corner of the vertebral body 2. Additionally, the cutout area and thus the distal end 108 also are configured with a plurality or more of teeth 107. The teeth 107 are configured and arranged so the teeth bite into the bony surface of the vertebral body when the corner of the vertebral body 2 is received within the cutout area of the guide sleeve distal end 108. Each guide sleeve is suitable about 20 cm in length, although suitable and preferred guide sleeve lengths can vary depending on the method of access.

The intervertebral spacing member 110 includes an intervertebral spacer 112 and an interconnecting member 114 that mechanically interconnects the cross member 104 and the intervertebral spacer 112. The interconnecting member 114 is secured to or retained by the cross member 104 so as to be maintained in fixed relation with respect to the pivots 106 for both guide sleeves 102. In an exemplary embodiment, the interconnecting member 114 is located at about the midpoint of the cross member 104 between the pivots 106. The interconnecting member 114 also is secured to the cross member 104 so the intervertebral spacer 112 is positioned between the distal ends 108 of the guide sleeves 102. More particularly, the interconnecting member 114 is positioned so the intervertebral spacer 112 is received within the distended disc space between the adjacent vertebral bodies 2.

In an exemplary embodiment, the interconnecting member 114 is in the form of a rod and the cross member 104 is configured with a through aperture 109 in which the rod is received. This configuration provides a mechanism by which the interconnecting member 114 is put into and maintained in fixed relation with respect to the pivot points 106. It is within the scope of the present invention for the cross member 104 to have any geometric shape, as well as being hollow or solid in construction, that is otherwise consistent for the intended use of the positioning jig 100.

The interconnecting member 114 also can be configured so as to prevent rotational motion of the interconnecting member with respect to the through aperture 109. For example, the rod and through aperture 109 may be configured so as to include a flat side in a portion of the circumference for the through aperture and the rod. Alternatively, the through aperture and rod may be arranged with a key and notch arrangement to prevent rotation.

When the guide sleeves 102 are secured to the cross member 104 and each guide sleeve distal end 108 mechanically engages the surface of the vertebral body 2, the guide sleeves are arranged so they maintain a consistent angle with respect to the vertebral body. Additionally, and in combination with the intervertebral spacer 112, this arrangement provides a three-point reference that ensures appropriate angles and alignment are maintained. Additionally, such a configuration establishes a condition whereby the positioning jig 100 locks down on the motion segment of the spine to be stabilized.

The use of the positioning jig 100 in the method of the present invention can be understood from the following discussion with reference to FIGS. 1–6. It shall be understood that as preparation for spinal fixation/stabilization, the medical personnel (e.g., surgeon) obtains access to the motion segment or structures to be stabilized or fused using any of a number medical/surgical procedures known to those skilled in the art. In this regard, this would involve such actions as preparing the disc space and performing retraction of vessels, muscles and nerves.

In this regard, it should be recognized that the method and positioning jig 100 of the present invention are particularly advantageous when performing a minimally invasive surgical procedure. The minimally invasive procedure can be performed through three holes, each about 1 inch across, in the abdomen and allows for the procedure to be executed without visualizing the vertebrae. Thus, and in contrast to a number of prior procedures, methods of the invention are not limited to an anterior presentation. Such methods of the invention also can be performed through a posterior, posteriolateral or pedicular approach.

In addition, when using a nitinol implant, the positioning jig 100 allows the implant to be properly positioned for and during insertion thereof. After gaining access, the surgeon also could scrape out the material from the failed disc or use this disc or its space as a reference point.

As preparation, the surgical personnel also select an intervertebral spacing member 110 that is appropriately sized, so it can accommodate the distended disc space. The intervertebral spacer 112 portion of the intervertebral spacing member 110 is inserted into the intervertebral space 4 between the adjacent vertebrae. In this way, the approximate center or mid point of, and the staring point on, the adjacent vertebrae to be fused or stabilized is thereby established or defined.

The intervertebral spacer allows the surgeon to maintain extremely accurate disk spacing. The intervertebral spacer also protects the spinal cord from accidental drilling or boring. If desired, the spacer can be made of bone and can be made with or without a through hole. The spacer design is suitably based on a construction that facilitates the selected technique for creating an arcuate aperture. An intervertebral spacer that is comprised of bone offers the advantage of being able to remain implanted following the procedure.

Other materials also can be suitably employed to form an intervertebral spacer. The placement of an implant provides a central axis through which a compressible, functional intervertebral disk member can be reliably secured. The artificial disk member suitably can be made from a variety of compressible materials, including e.g. silicon, elastomeric polymers, polyurethanes and copolymers thereof, hydrogels, collagen or bioabsorbables.

Next, the positioning jig 100 is locked down on top of the motion segment to be immobilized, as more clearly shown in FIG. 2. In this regard, the surgical personnel slide the interconnecting member 114 of the intervertebral spacing member 1110 into an aperture 109 provided in the cross member 104. In this way, the aperture 109 in the cross member 104 positions the intervertebral spacing member 110 between the distal and proximal ends of the drilling guides 102. Although illustrated as being located in the mid-point, the intervertebral spacing member can be centrally located or offset to either side to enable drilling of holes in the vertebrae laterally against the spine.

Preferably, the aperture 109 in the cross member 104 is configured so as to prevent the cross member 104 or intervertebral spacing member 110 from rotating with respect to each other. For example, a portion of the aperture 109 and a portion of the interconnecting member 114 is flattened so as to pre-define a given orientation. Alternatively, the aperture 109 is configured with a notch or keyway and the interconnecting member 114 is configured with a key or protrusion that is received in the keyway.

As provided above, the distal end 108 of each guide sleeve 102 is preferably configured so each distal end mechanically engages the surface of the vertebrae 2. In the illustrated embodiment, the distal end 108 is arranged with a cutout area that is designed to accept the corner of the vertebrae 2 as more clearly illustrated in FIG. 3. As also shown in FIG. 3, the cutout area is provided with a plurality of teeth 107 that bite into the bony surface of the vertebrae 2. It is within the scope of the present invention for the guide sleeve distal end 108 to be disposed at other positions on the surface of the vertebrae 2 such as that illustrated in FIG. 6A.

After locating the positioning jig 100 with respect to the motion segment to be fused, the surgical personnel secure the guide sleeves 102 at each of the pivots 106. This advantageously ensures that the appropriate angles and alignment of the guide sleeves 102 with respect to the vertebrae 2 are maintained as well as locking the positioning jig 100 down on the motion segment to be fused.

As noted above, an initial through hole is formed in each vertebrae 2 by any of a number of methods, e.g. by a drill, by ablation of the material comprising the vertebrae using an energy source such as RF, ultrasonic waves, cryogenics and water jets or by any other means known to those skilled in the art and which can be adapted for use with the positioning jig 100 of the present invention. For purposes of describing the present invention, however, the following discussion is simplified to describing the method in terms of drilling the initial aperture or initial through hole 6 in the vertebrae 2. This, however, shall not be inferred as being a limitation on the method according to the present invention to only drilling.

A fixed or flexible drill bit 150 is inserted into and down each drill guide 102 so the ends thereof contact the surface of the vertebrae 2. The surgical personnel operate the drill bits in accordance with accepted techniques so as to create an initial through hole 6 in each of the vertebrae. Preferably, and as shown in FIG. 3B, the through holes 6 being created are intersecting with convergent paths within the intervertebral space 4. In other words, the projection of the long axis for each of these through holes 6 intersects so the vertex created by intersection of the long axes is located within the intervertebral space 4.

The initial through hole 6 initially formed in each vertebrae 2 has a diameter much less than that of the implant 160 that is to be used to stabilize or fuse the motion segment. After forming the initial through hole 6, the surgical personnel insert a guide wire 170, such as a 0.093 inch nitinol guide wire, into and down one guide sleeve 102 and through the through hole in one vertebrae 2. The surgical personnel continue to push the guide wire 170 across the intervertebral space 4 and into the through hole 6 in the other vertebrae as more clearly illustrated in FIGS. 3C–D. In a particular embodiment, the guide wire 170 is configured with a slightly curved tip. The guide wire 170 is generally in a curved configuration when disposed in the through hole 6 of the vertebrae 2.

Figure 3B:
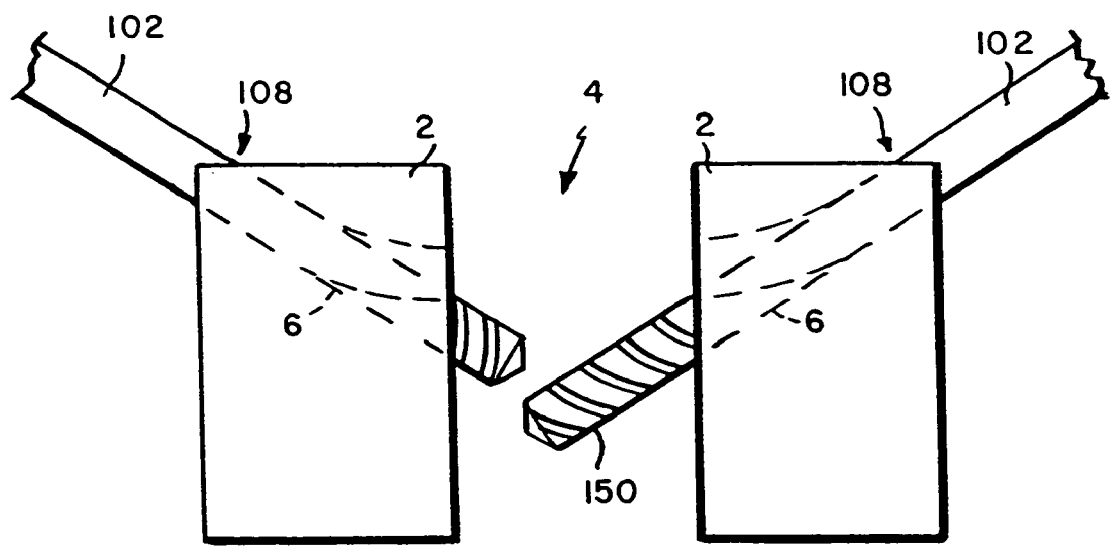
Figure 3C:
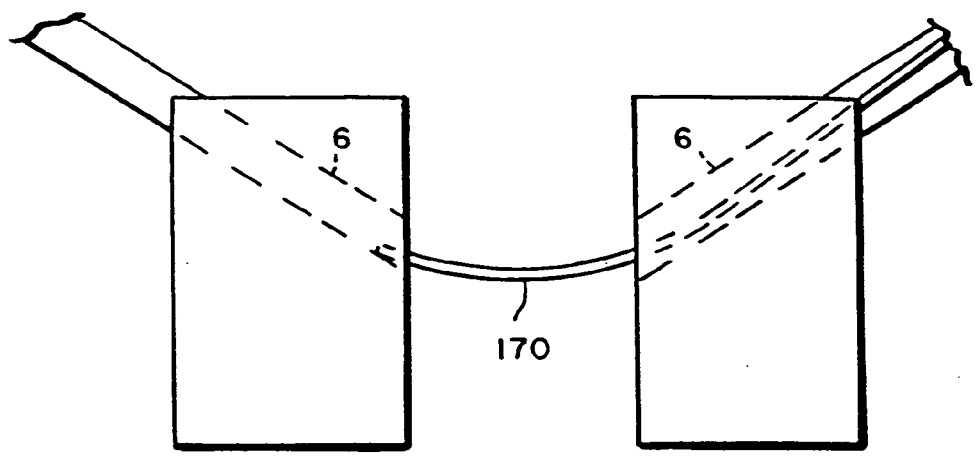
Figure 3D:
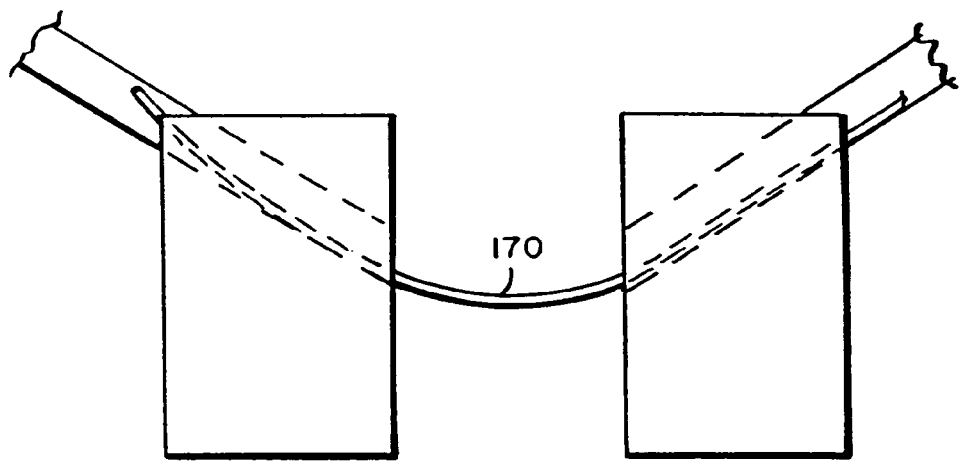
Figure 3E:
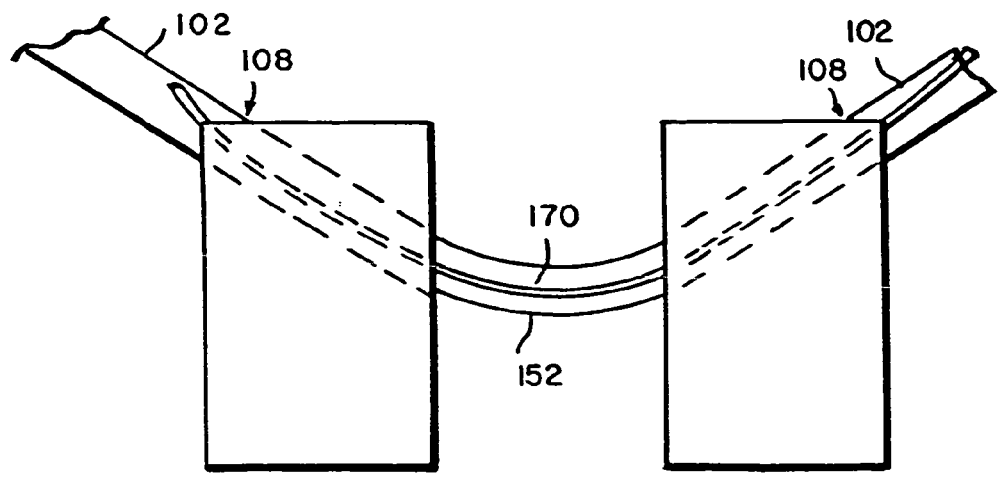

A flexible/curved drill bit 152 is then passed through one of the guide sleeves 102 and over the guide wire 170 so as to form a curved through aperture 6a in each of the vertebrae as shown in FIG. 3E. The curved or arcuate through aperture 6a is formed with a cross-section that complements the cross-sectional shape of the implant 160. Preferably, the arcuate through aperture is sized to be slightly smaller than that of the implant 160 so there is a friction, snug or interference fit between the implant 160 and the arcuate through aperture 6a.

In this way, when the implant 160 is inserted into the arcuate through aperture 6a, it will remain therein without further need of screws or other artifacts or devices for securing the ends of the implant to each vertebrae 2. It is within the scope of the present invention, however, for screws or other devices be provided as an additional measure or protection for securing the implant 160 within the vertebrae 2.

Figure 4A:
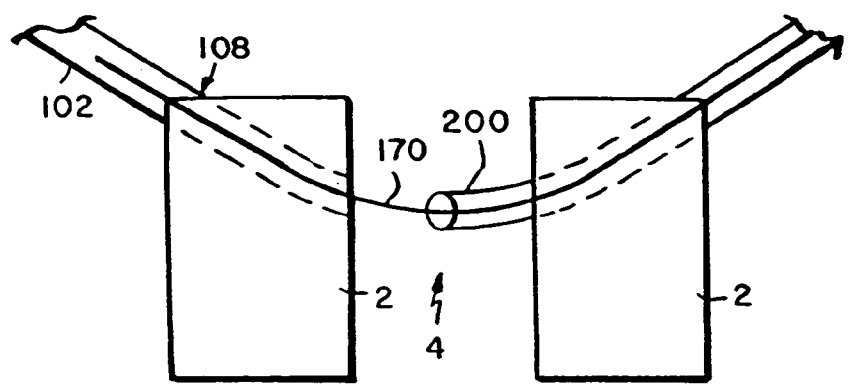
FIGS. 4A and 4B are schematic views that illustrate alternate ways of making a hole in each vertebral body.
Figure 4B:
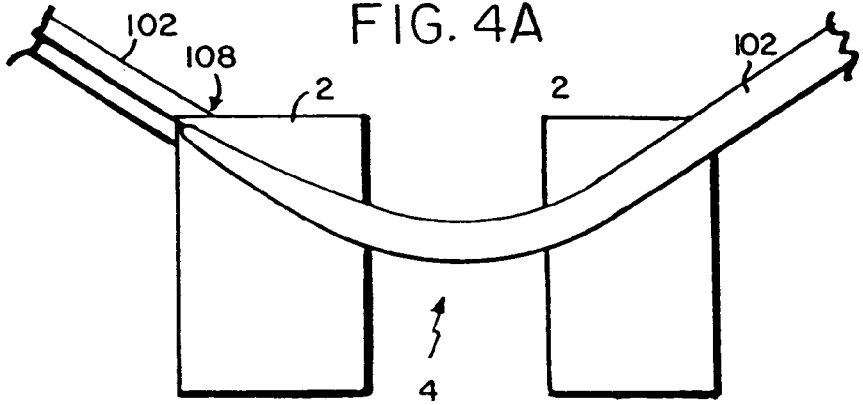
Figure 4C:
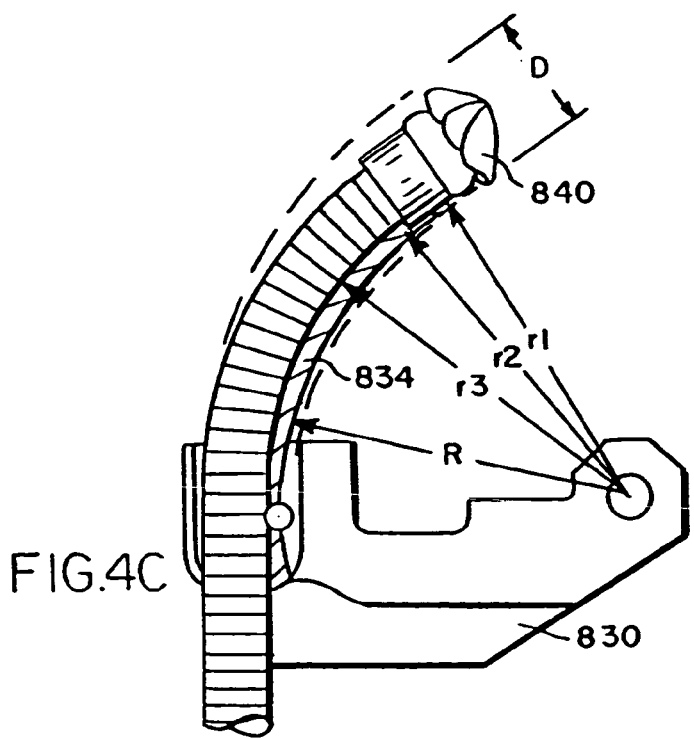
FIG. 4C is a plan view of a Romano device for making a curved hole. Shown is one of the two opposed curved cutter guides and a flexible cable having a cutting bit attached to one end.

Alternatively, the curved or arcuate through aperture 6a is formed using any of a number of other techniques as described below. In one case, and as shown in FIG. 4A, the arcuate through aperture 6a is formed in the vertebrae 2 by using a flexible reamer 200. The flexible reamer is run or passed over the guide wire 170 to ream or core out the arcuate through aperture 6a. The cancellous bone of the vertebrae 2 is relatively soft so that it is possible to use a reamer to core the hole aperture. Similarly, and as shown in FIG. 4B, a curved awl or a progressively larger guide wire 170a can be used to punch a curved hole in the vertebrae. FIG. 4C shows a Romano device suitable for drilling a curved bore such as that disclosed in U.S. Pat. No. 5,700,265 the teachings of which are incorporated herein by reference. A swing arm 830 and curved guide arm 834 navigate the drill bit 840 through a defined radius of curvature.

In addition to the mechanical devices for drilling, punching or reaming out the arcuate through aperture 6a, the discharge end of an energy source, such as RF, ultrasonic, cryogenic, laser and water, can be located within the guide sleeve 102 and passed over the guide wire so as to form the arcuate through aperture. For example, the nozzle(s) of a high pressure water source can be arranged so the discharging or ice crystal water impinges on the bony material of the vertebrae 2 and the material is thereby ablated away to form the arcuate through aperture 6a. Similarly, laser light, RF waves or ultrasonic waves can be focused on the bony material within the vertebrae 2 to form the arcuate through aperture 6a.

The foregoing describes the formation of the arcuate through aperture 6a that receives the implant 160 by passing a mechanism from the entrance to the exit of the initially formed through hole 6. It is within the scope of the present invention, for a guide to be located within the intervertebral space 4 so the curved through aperture is formed by drilling from the intervertebral space out, rather from the outside in.

Figure 2B:
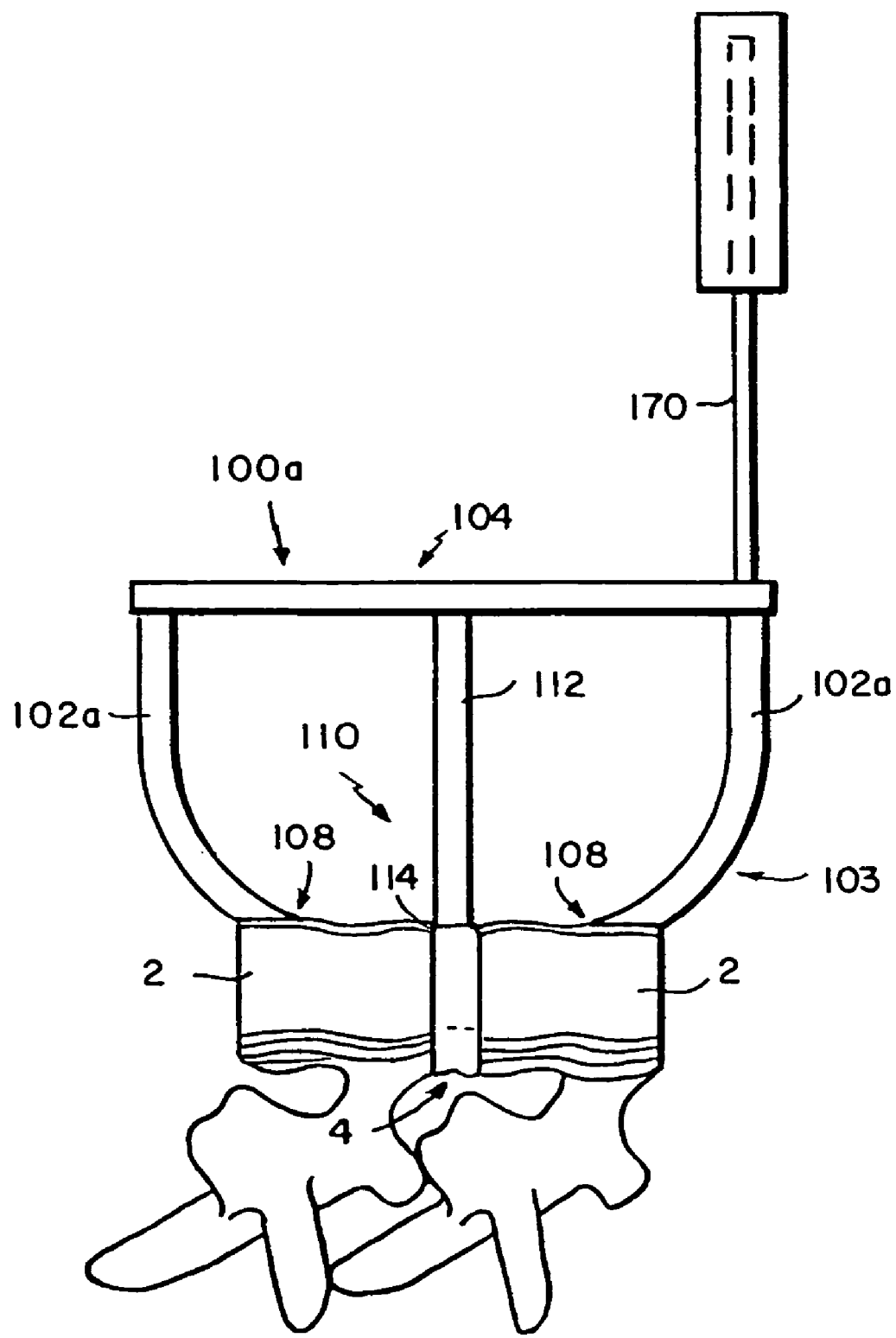
FIG. 2B is a schematic view of an alternative positioning jig according to the present invention disposed about two vertebral bodies.

There is shown in FIG. 2B a schematic view of an alternative positioning jig 100a that is disposed about two vertebral bodies. This alternative positioning jig 100a is similar to the positioning jig 100 of FIG. 2A except for the guide sleeves. As such reference shall be made to the foregoing discussion regarding FIGS. 1–2A for further details as to the common features for these two positioning jigs 100, 100a. In the illustrated embodiment, a guide wire 170 is being inserted into one of the guide sleeves 102a and is configured so that the proximal end of the guide wire 170 is arranged so as to include an impact fitting to protect the guide wire about the proximal end.

In the alternative embodiment, the guide sleeves 102a are tubular members that are configured so that at least a portion 103 of each guide sleeve is arcuate. In the illustrated embodiment, the arcuate portion 103 of the guide sleeve 102a is proximal the vertebral body such that one end of the arcuate portion comprises the distal end 108 of the guide sleeve that is in contact with the vertebral body 2. It is contemplated, however, that the guide sleeve can be configured so as to be substantially arcuate between the vertebral body 2 and the cross member 104.

The arcuate shape provides a convenient mechanism that can simplify the above-described process for making an arcuate through hole 6a in the vertebral body 2. The arcuate shape also provides a mechanism to orient the tool, device or apparatus being inserted into the guide sleeves 102a, for example the drill or high energy source for forming the initial through hole, so use of the tool etc. is more convenient to the surgical personnel performing the procedure.

After the arcuate through aperture 6a is formed, then the implant 160 is inserted therein so it is disposed within the through aperture 6a in one vertebrae 2, passes or extends across the intervertebral space 4 and disposed within the through aperture 6a of the other vertebrae. The implant 160 is made from any one or more suitable materials such as e.g. a metal such as titanium or stainless steel, bone, bone with bone morphogenic protein, carbon fiber composite, nitinol. The implant being inserted into the final aperture is made from one or more of a metal (e.g., titanium or stainless steel), bone, morphogenic protein (including a combination of bone and bone morphogenic protein), carbon fiber composite, nitinol or biodegradable materials such as polyactic acid or polyglycolic acids and copolymers and other derivatives thereof, or collagen and collagen coated metal or bone. The implant also may comprise an in situ-formed plug where the aperture acts as a mold for an epoxy or other polymer-based system. The implant, preferably is curved so it generally conforms to the radius of the arcuate through apertures 6a in each vertebrae 2, however, other geometric shapes are contemplated that are consistent with the intended use including straight members.

The implant 160 suitably can be provided with a circular or oval shape. The diameter or width of the implant can vary over a relatively broad range and may depend on the size of the vertebrae and desired implant stiffness. More specifically, in preferred embodiments, the implant may suitably range in diameter or width from about 5 mm or as small as is mechanically sufficient, to sizes approaching that of large intramedullar rods, or about 22 mm. Preferably the implant should have a diameter or width from about 7 to 12 mm, more preferably about 9 mm. The implant also preferably should have an appropriate radius of curvature such that both vertebrae are engaged while staying well clear of the spinal cord. That radius preferably is about 1.5 inches, as referenced from the arcuate implant's inner radius.

The implant 160 is suitably a solid or hollow (e.g., tubular) member. The implant can be suitably configured so as to have fenestrations 166 (FIG. 6A) that allow biologic elements of bone to traverse through it or across it, thereby enhancing potential for stability and for cross-segmental healing. In particular, the implant 160 can have cutting fenestrations similar to a cheese grater, allowing fragments of bone to be pared off as the implant 160 is being inserted into the through apertures in either vertebrae. A fenestrated implant 160 that is hollow can be filled with bone chips or synthetic or engineered bone healing materials, allowing for bone ingrowth, and a cheese grater type of implant with cutting fenestrations can add freshly pared fragments of bone to the packed bone chips or other materials to enhance bony ingrowth. Additionally, the fenestrations 166 can be surface dimples, sharpened edges, cutting indentations or other alterations in the exterior surface of the implant 160 to enhance or further ensure the secure fitting of the implant into the arcuate through aperture 6a as well as for facilitating bone growth.

Figure 5A:
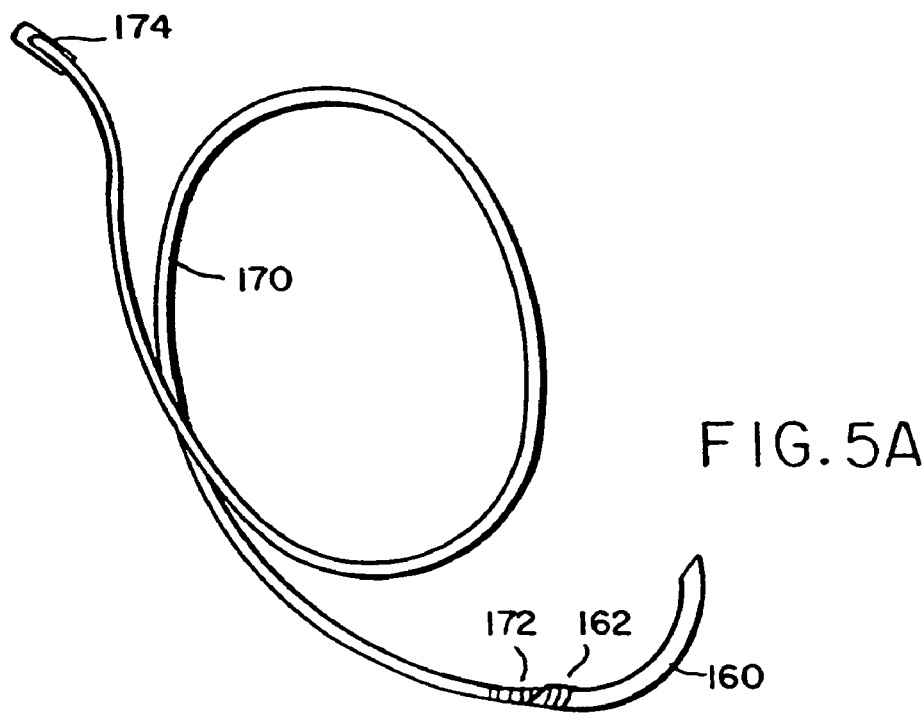
FIG. 5A is a schematic view of one device for implanting the fixating member.

The particular technique for inserting the implant 170 into the through aperture 6a of a vertebrae 2 for fixing of the movable segment is dependent upon the material used to make the implant. For an implant 160 made from titanium, and as shown in FIG. 5A, a threaded end 162 (e.g., a female threaded end) is provided at one end of the titanium implant 160 for threaded engagement with the threaded counterpart (e.g., male counterpart) at one end 172, the distal end of the guide wire 170. This can be accomplished for example by removing at least one of the guide sleeves 102 from the entrance opening of one through aperture 6a so the threaded end 172 of the guide wire is exposed. The implant threaded end 162 is then screwed onto the guide wire threaded end 172 and the so tethered end 162 of the implant 160 is positioned at the entrance opening of the through aperture 6a and pulled into place by pulling on, for example, the proximal end 174 of the guide wire 170.

Preferably, the distal end 108 of one guide sleeve 102 remains engaged at the entrance opening for the other through aperture 6a, so as to serve as a bearing surface or brace for the guide wire 170 as it is being pulled out of this entrance opening. This is done to keep the guide wire 170 from cutting through the cantellous bone when the guide wire is under tension because of the pulling action. Alternatively, a tubular member with a rounded surface may be advanced over the guide wire and through the remaining guide sleeve 102, to ensure that the guide wire pulls from the appropriate angle. This technique is suitable for use with metallic and other rigid material type of implants.

Figure 5B:
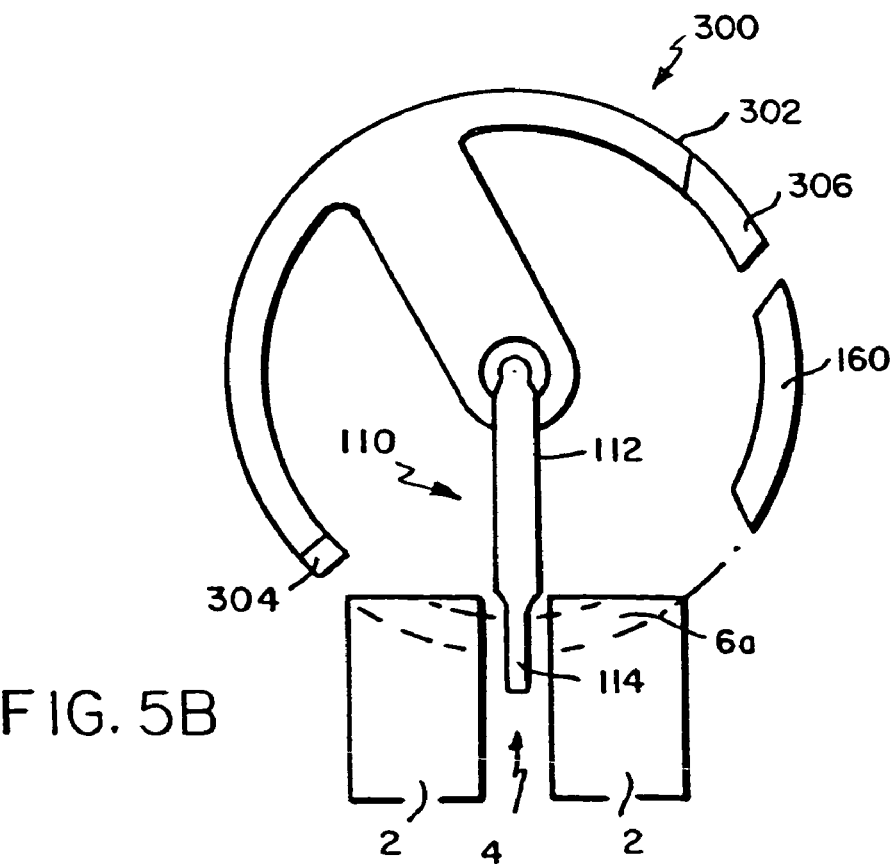
FIG. 5B is a schematic view of alternate device for implanting the fixating member.

Alternatively, and as shown in FIG. 5B, a pushing mechanism is useable for inserting or tamping the implant 160 into the arcuate through apertures 6a. In the illustrated embodiment, an arcuate pushing mechanism 300 is configured so as to rotate about an axis of rotation that corresponds generally to the center of the circle subscribed by the arcuate through apertures 6a. The arcuate pushing mechanism applies a force to the distal end of the implant 160 so as to drive the proximal end of the implant through the arcuate through aperture 6a in one vertebrae, across the intervertebral space 4 and into the arcuate through aperture 6a of the other vertebrae 2.

In the illustrated embodiment, the positioning jig 100 is removed except for the intervertebral spacing member 110 or bone interverterbral spacer where the intervertebral spacer 114 remains disposed in the intervertebral space 4. The arcuate pushing mechanism 300 is attached to the end of the interconnecting member 112 by means of a jig or other member or device so the pushing mechanism can rotate about the end of the interconnecting member. In this way, the arcuate arm 302 of the pushing mechanism 300 can be advanced by having one of the surgical personnel rotating it about its axis of rotation. Alternatively, or in addition, the surgical personnel can strike one end 304 of the arm 302 with a mallet or other weighted object so as to drive the implant 160 into the through aperture 6a. For example, striking may be required near the end of the insertion process when there is maximum friction being developed on the inserted implant. The arm 302 also may be configured with a curved support sleeve 306 in which the implant is received.

Figure 6A:
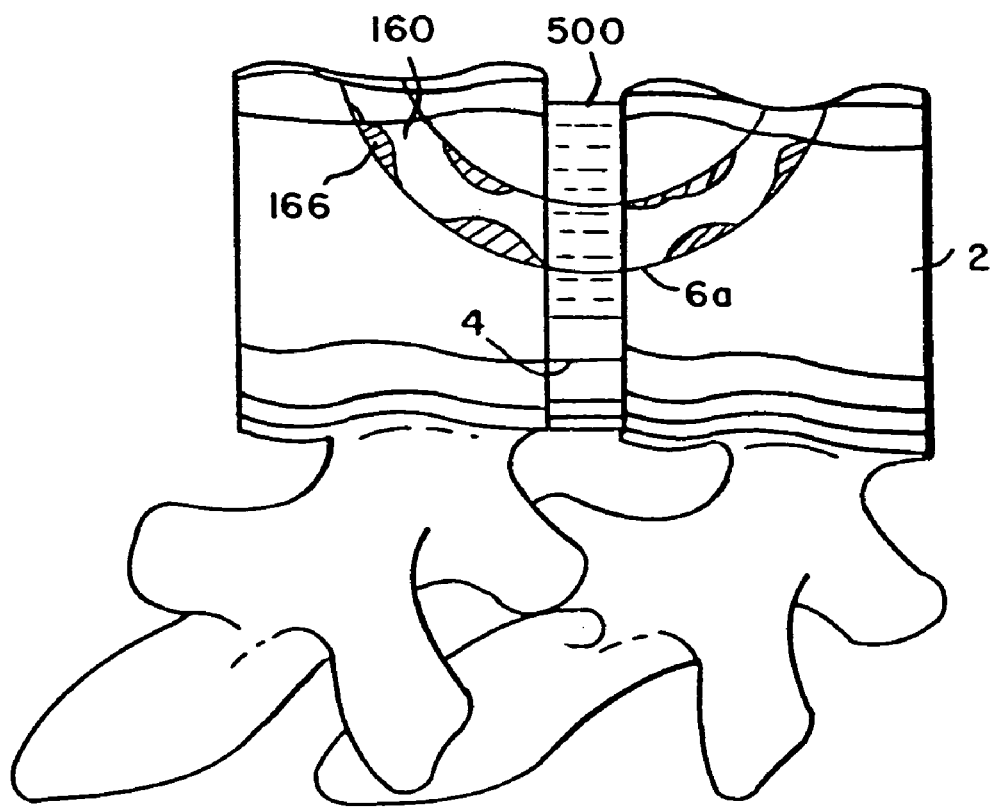
FIG. 6A is a schematic view of the vertebral bodies illustrating the implantation of the fixating member in the holes.
Figure 6C:
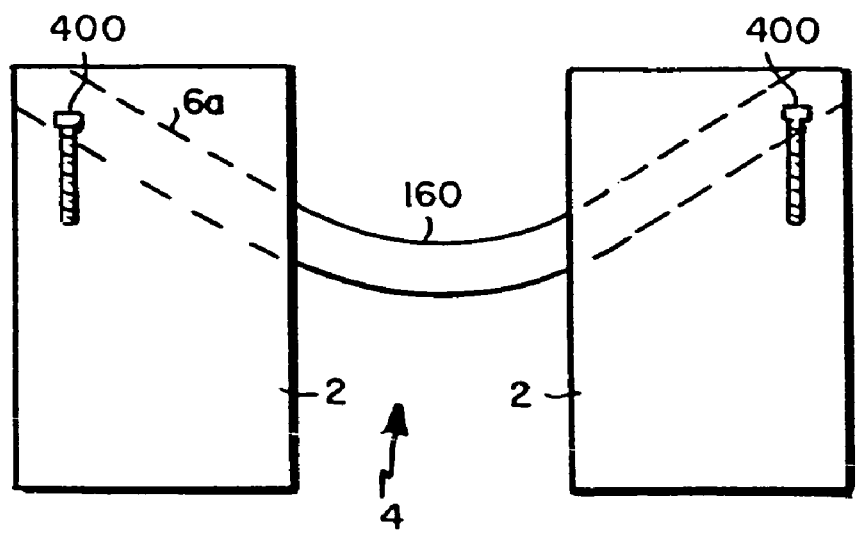
FIG. 6C is a schematic view of the vertebral bodies to illustrate securing of the fixating member.

Although the implant 160 and through apertures 6a are sized so that there is preferably at least a snug-fit therebetween, as an extra measure of protection, the implant 160 may be further secured in place at its ends by means of screws 400 as shown in FIG. 6C. Alternatively, the implant 160 may be secured in place by a plate, screw, staple or a combination thereof. Additionally, the implant can be arranged so as to include a biting or expansion element(s) that can be driven out in a lateral direction so as to engage the bony structure of the vertebrae 2.

As provided above, and as shown in FIGS. 7A–B, the implant 160a can be made from nitinol. A nitinol implant 160a is advantageous in that a curved nitinol implant can be straightened as shown in FIG. 7B prior to insertion into the arcuate through apertures 6a. The straightened nitinol implant 160a can be advanced down one of the guide sleeves 102 in any of a number of ways, for example, by pushing or pulling, so it can be driven into the arcuate through apertures 6a. The nitinol implant 160a also can be inserted into the arcuate through apertures 6a in any of the other fashions described above in connection with FIGS. 5A–B.

Additionally, a sharp edge of the nitinol implant can be used like a reamer or awl to thereby enlarge the initial through hole 6 as the implant is being inserted or driven into the initial though aperture. This avoids the intermediate step of drilling or otherwise forming the arcuate through aperture 6a before insertion of the implant.

FIG. 7C depicts an illustrative device 400 for inserting a nitinol implant 160a, which device includes a guide tube 402 and a pusher 404. The distal end 408 of the guide tube 402, similar to the positioning jig guide sleeve distal end 108 is preferably configured so as to be capable of releasably mating with a surface, or portion thereof, of the vertebrae 2 where the entrance of the arcuate through aperture 6a is located. In the illustrated embodiment, the guide tube distal end 408 is configured with a cut out so as to receive a corner of the vertebrae 2 therein.

The distal end 408 is disposed on the vertebrae so that the lumen therein is aligned with the arcuate through aperture 6a. The straightened nitinol implant 160a is inserted into the guide tube 402 along with the pusher 404 such that the distal end of the pusher is in contact with the proximal end of the nitinol implant. The pusher distal end 408 mates with the implant proximal end so as to maintain the orientation and direction of the nitinol implant 160a within the guide tube 402 so that it curves in the proper direction when it exits the guide tube. Alternatively, and as shown in FIGS. 8A–B, the orientation of the nitinol implant 160a within the guide tube 402 is maintained with a flat side or with a key and notch type of arrangement.

The pusher 404 includes a stop 406 to limit the travel of the pusher within the guide tube 402. This in turn limits the amount of travel by the nitinol implant 160a so as to assure that the implant remains buried within the vertebrae and not exposed above the surface thereof.

The placement of the implant according to the systems and methods of the present invention is advantageous in that the inserted implant resides completely within the vertebrae and, thus, within the spine, with no protrusion as compared with prior art devices. The implant and its placement provide a configuration which allows for some compression and cantilever force, but deters rotation and sheer. Additionally, in the present device, the moment arm is more centrally located within the spine as compared to prior devices. This central location also provides better stability in the face of torsion as compared to prior art devices.

In general, the placement of an arcuate implant within the arcuate through apertures as described herein is particularly advantageous because the implant is buried to avoid contact with neurovascular structures. The placement provides load sharing and thus provides a better healing bio-mechanical environment and also provides a more advantageous fixation to avoid mechanically sub-optimal stresses. Also important, this method allows securement and avoids displacement of a spinal fusion or disk replacement device without modification or damage to the vertebrae's load bearing surface. Rather, one or two holes placed in or around the center of a vertebrae can be sufficient. The method and positioning jig 100 of the present invention also are advantageous in that the jig can be adapted for use in minimally invasive procedures. Additionally, the capability to position implants in accordance with the methods described herein enables avoiding blood vessel injury, erosion into organs and damage to adjacent nerves. This provides a significant advantage over presently existing technologies for disorders of the spine including fractures, arthritis, deformity, infections, tumor and mechanical spinal disorders.

Although the foregoing method describes extending a single implant between adjacent vertebrae this description should not be construed as being a limitation as one or more implants can be positioned across each motion segment as described herein.

In addition, the above described method can be further adapted so as to be used to secure an intravertebral prosthetic device 500 (i.e., artificial disc) such as that shown in FIG. 6A. According to this aspect of the invention, the implant is made partly or wholly from a flexible material such as silicon, elastomeric polymers, polyurethances and copolymers thereof, hydrogels, collagen, bioabsorbables, compositions, or a metallic spring or coil, so as to allow continual mobility between the vertebral bodies. One or more arcuate implants are provided which pass through a partial or complete hole in the prosthesis. This effectively prevents the prosthesis from becoming dislodged as well as maintaining its location and orientation within the disc space.

There is shown in FIGS. 17A–C exemplary arcuate implants 160b–d for use in securing the intravertebral prosthetic device 500 within the bones of the spine. Referring now to FIG. 17A, there is shown an arcuate implant 160b having a first section 163 disposed between two end or second sections 165 that mechanically engage the first section. The first section 163 is made up of a compressible material and the second sections 165 are made up of a material(s), such as metals and bone, that is conducive to the attachment of the second sections to the bone thereby securing the implant 160b. Alternatively, and as shown in FIG. 17B, the implant 160c can comprise a first section 163 that is bonded or otherwise mechanically secured to the second sections 165.

The implants 160b, c of either FIGS. 17A, B extends through an aperture or hole in the prosthetic device 500 and into the vertebral bodies adjacent to the prosthetic device similarly to that illustrated in FIG. 16A. Additionally, the first section 163 of either of the two implants 160b,c is arranged so as to extend through the prosthetic device 500. See also the discussion above for FIG. 16A for other aspects of securing the prosthetic device (e.g., one or more apertures in the prosthetic) and materials for the implant.

Figure 6B:
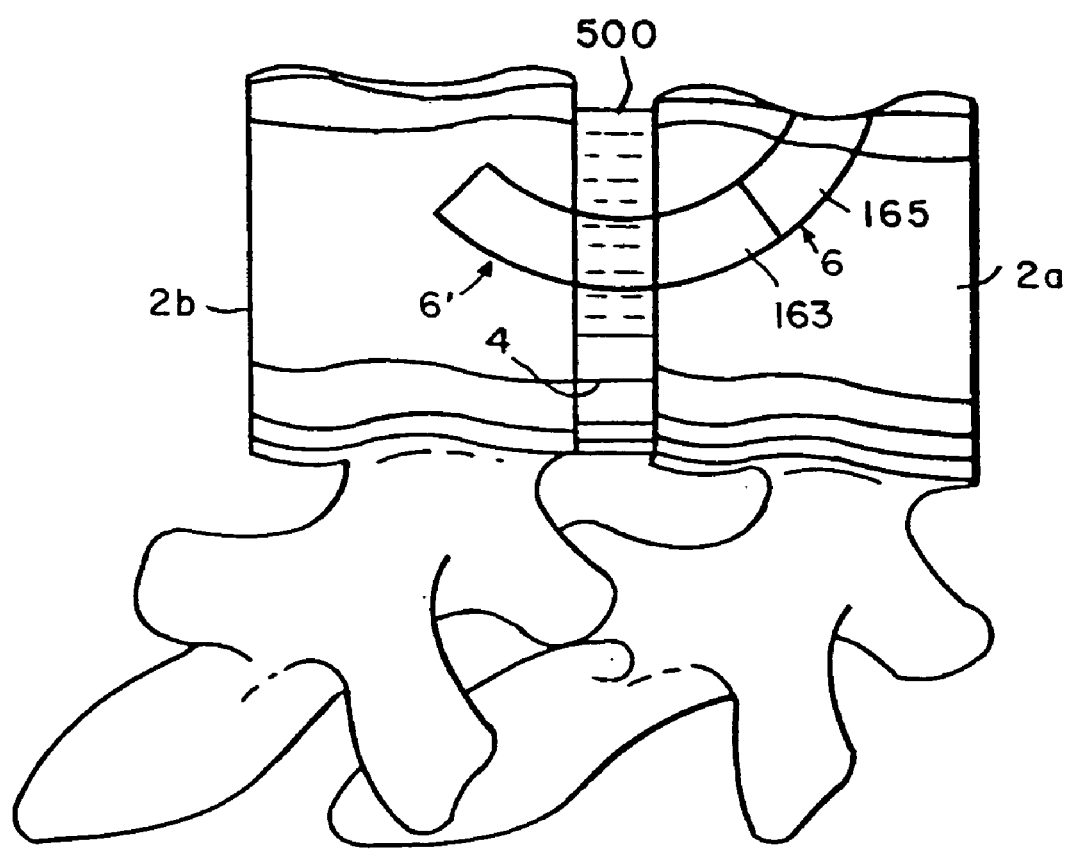
FIG. 6B is a schematic view of the vertebral bodies illustrating another form of implantation of the fixating member in the holes particularly for securing an intravertebral prosthetic device.

The above described method also can be further adapted so as to be used to secure an intravertebral prosthetic device 500 (i.e., artificial disc) according to another technique such as that shown in FIG. 6B using an implant, such as the exemplary implant 160d shown in FIG. 17C. In this technique any of the mechanisms and methods described herein are used to form at least an aperture 6, preferably an arcuate through aperture, in one adjacent vertebral body 2a. More particularly, the aperture forming mechanism or method also forms another aperture 6' in the other adjacent vertebral body 2b. This another aperture 6' in the other vertebral body 2b is not a through aperture but rather only extends only into a portion of the other vertebral body. After forming the apertures 6, 6', the prosthetic device 500 is disposed in the disc space or intervertebral space 4. The implant 160d is then pressed into and through the aperture 6, through the prosthetic device 500 and intervertebral space 4 and into the aperture 6' of the other adjacent vertebral body 2b.

The exemplary arcuate implant 160d shown in FIG. 17C includes a first section 163 and a single second section 165 that mechanically engages the first section as shown in FIG. 17A or is bonded or other wise mechanically secured to the first section as shown in FIG. 17B. Reference shall be made to the above discussion regarding FIGS. 17A,B for further details regarding the make up and materials of the first and second sections 163, 165 and the discussion for FIG. 16A for other aspects of securing the prosthetic device (e.g., one or more apertures in the prosthetic) and materials for the implant.

Figure 9:
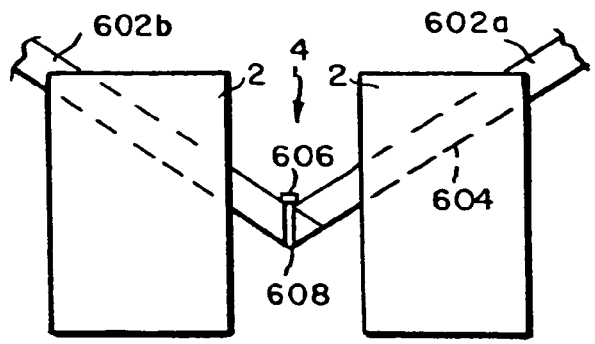
FIG. 9 is a schematic view of the vertebral bodies with a fixating member according to a second aspect of the present invention.

FIG. 9 shows a method for inserting an implant 600 according to a second aspect of the present invention. A final through aperture 604 is formed in each of the vertebrae in accordance with above described techniques such as by drilling. Except that the through aperture 604 that receives the implant can be straight as shown in FIG. 9 or can be arcuate as shown in any of FIGS. 3–6. As such, reference should be made to the foregoing discussion for further details regarding the formation of the final through aperture 604.

In the method according to the second aspect, the implant is in two sections 602a,b. The proximal ends 608 of the two sections 602a,b are particularly configured so they can be mated to each other and interlocked to each other by means of an interference fit, a nut and bolt, a screw or a pin 606. Thus, to fix the moveable segment, one section 602a is inserted into the through aperture 604 in one vertebrae 2 and the second section 602b is inserted into the through aperture 604 of the other vertebrae. The two sections 602a, b are inserted into their respective through apertures until the proximal ends 608 thereof are mated to each other. The pin 606 or other securing mechanism is then used to interlock the proximal ends and thus form a rigid implant. Although the sections are illustrated as being straight, it is within the scope of the present invention for the sections to arcuate so as to form an interlocking rod when assembled.

Figure 10:
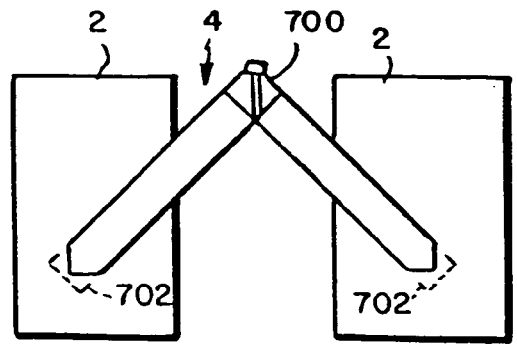
FIG. 10 is a schematic view of the vertebral bodies with a fixating member according to a third aspect of the present invention.

FIG. 10 shows a method for inserting an implant 600 according to a third aspect of the present invention. According to this method, the apertures 702 in each vertebrae 2 are formed so they extend from the vertebral space 4 outwards, penetrating into the cancellous bone. In this aspect, the apertures 704 formed in the vertebrae need not be through apertures. The implant 600 is like that described above for the second aspect of the present invention except that it is inverted from that shown in FIG. 9.

Figure 11A:
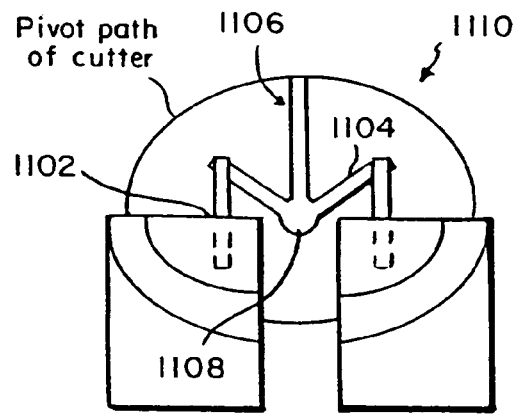
FIG. 11A is a schematic view of a cutter bracket system according to the present invention.

There is respectively shown in FIGS. 11A, B a cutter bracket system 1100 and a curved bit or drill system 1120, the curved drill system being for use with such a cutter bracket system. The cutter bracket system 1100 and curved drill system 1120 comprises another embodiment of the present invention for forming arcuate apertures 6a (FIG. 6A) in each of the adjacent vertebral bodies 2. Referring now to FIG. 11A, the cutter bracket system includes temporary vertebral screws 1102, pivot brackets 1104 and a pivot arm 1106. In the illustrated embodiment, there is two temporary vertebral screws 1102 that are each secured to the adjacent vertebral body 2 that is to be fused, however, this shall not be construed as a limitation on the number of intervertebral screws. Extending from the temporary vertebral screws 1102 are the pivot brackets 1104, which locate the pivot point 1108 with respect to the adjacent vertebral bodies 2 and maintian the pivot point in this orientation. The pivot arm 1106 is rotatably mounted to the pivot brackets 1104 using any of a number of mechanisms or techniques known in the art so that the pivot arm pivots or rotates about the pivot point 1108. In an exemplary embodiment, the temporary vertebral screws 1102, the pivot brackets 1104 and the pivot arm 1106 are made from stainless steel although other materials are contemplated.

Figure 11B:
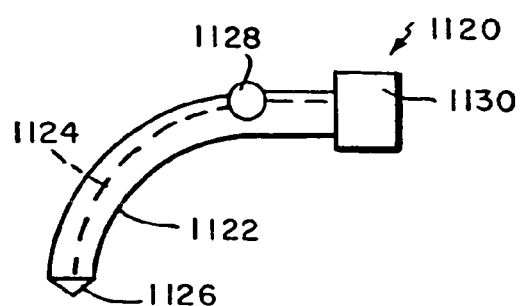
FIG. 11B is a schematic view of a curved drill used with the cutter bracket system of FIG. 11A.

The drill system illustrated in FIG. 11B includes a curved cannula 1122, a flexible cable 1124, a cutting head or burr 1126 and a motor 1130. The flexible cable 1124 is rotatably disposed with the curved cannula 1122. One end of the flexible cable 1124 is attached to the cutting burr 1112 and the other end of the flexible cable 1124 is attached to the motor 1130, whereby the motor drives the cutting burr so it to rotates in the desired manner. In the illustrated embodiment, the motor 1130 also is mounted to an end of the curved cannula 1122. In an exemplary embodiment, the curved cannula 1122 is made from stainless steel and the flexible cable 1124 is a flexible, teflon coated stainless steel cable, the cutting burr 1126 is made from stainless steel, although it is within the scope of the present invention for other materials to be used.

The motor 1130 includes any of a number of devices known in the art that develop or provide a rotary output which can be used to rotate the flexible cable 1124, such devices include, but are not limited to, electric or pneumatic drills, DC/AC electric motors, or, pneumatic, air driven rotary motors. It also is within the scope of the present invention for the drill system 1120 to further include a coupling member, as is known in the art, that operably and rotatably interconnects the flexible cable 1124 and the motor 1130 such that the motor is located remote from the curved cannula 1122. In this way, any of a number of rotary devices such as a drill, that are readily available, can be adapted for use in the drill system 1120 of the present invention and interconnected to the flexible cable 1124 by means of the coupling member.

The drill system 1120 is mounted or attached to the pivot arm 1106, distal from the pivot point 1108, by means of a connector 1128 on the curved cannula 1122. The connector 1128 and the corresponding feature on the pivot arm 1106 comprises any of a number of mechanisms or devices known in the art (e.g., clamp type mechanism) by which the curved cannula can be removably secured to the pivot arm so there is essentially no relative movement therebetween. In a particular embodiment, the curved cannula 1122 is secured proximal to or at the distal end of the pivot arm. In this way when the drill system 1120 is secured to the cutter bracket pivot arm 1106 and the cutter bracket pivot arm 1106 is rotated about the pivot point 1108, the pivot arm guides the curved drill system, in particular the cutting burr 1126 on a well-defined circular path.

In use, the cutter bracket system 1110 is temporarily secured to the adjacent vertebral bodies 2 to be fused by the temporary vertebral screws 1102. In particular, the cutter bracket system 1110 is secured to the vertebral bodies 2 so that the pivot point 1108 is positioned so as to be spaced from a surface of the vertebral bodies and so as to be between the adjacent vertebral bodies, more particularly at about the midpoint of the intervertebral space 4. After securing the cutter bracket system to the vertebral bodies the curved drill system 1120 is mounted to the pivot arm as described above.

The pivot arm 1106 is then rotated in one direction, for example a clockwise direction, about the pivot point 1108. As the pivot arm 1106 is rotated thereabout, the cutting burr 1126 is operated so the drill system 1120 drills an arcuate hole in the vertebral body 2 on one side of the pivot point. The curved drill is then remounted so the cutting burr 1126 is on the other side of the pivot point 1108 and the pivot arm is rotated in a counter clockwise direction so the drill system 1120 drills an arcuate hole in the vertebral body 2 on the other side of the pivot point 1108. In an exemplary embodiment, the arcuate hole is completely formed when the pivot arm 1106 bottoms out or contacts the vertebrae being drilled. After forming the arcuate holes, the curved drill system 1120 is dismounted from the pivot arm 1106 and the cutter bracket system 110 is disconnected from the adjacent vertebral bodies 2. In this way, two matched arcuate holes are formed in the adjacent vertebral bodies 2 that are sized and configured to receive an arcuate implant being inserted therein. Reference shall be made to the foregoing discussion for further details regarding such an arcuate implant or fixation member.

Although the foregoing describes the formation of the arcuate holes or apertures 6*a* in the adjacent vertebral bodies 2 using a curved drill system 1120 mounted to the pivot arm 1106, this shall not be construed as a limitation. As discussed hereinabove, it is within the scope of the present invention for other devices, mechanism or techniques, such as the above-described ablation energy sources, to be adapted for use with a rotating pivot arm 1106 to form the through holes/apertures 6*a*. As such these other devices, mechanisms or techniques are contemplated for use with the above-described cutter bracket system.

Figures 12A, 12B:
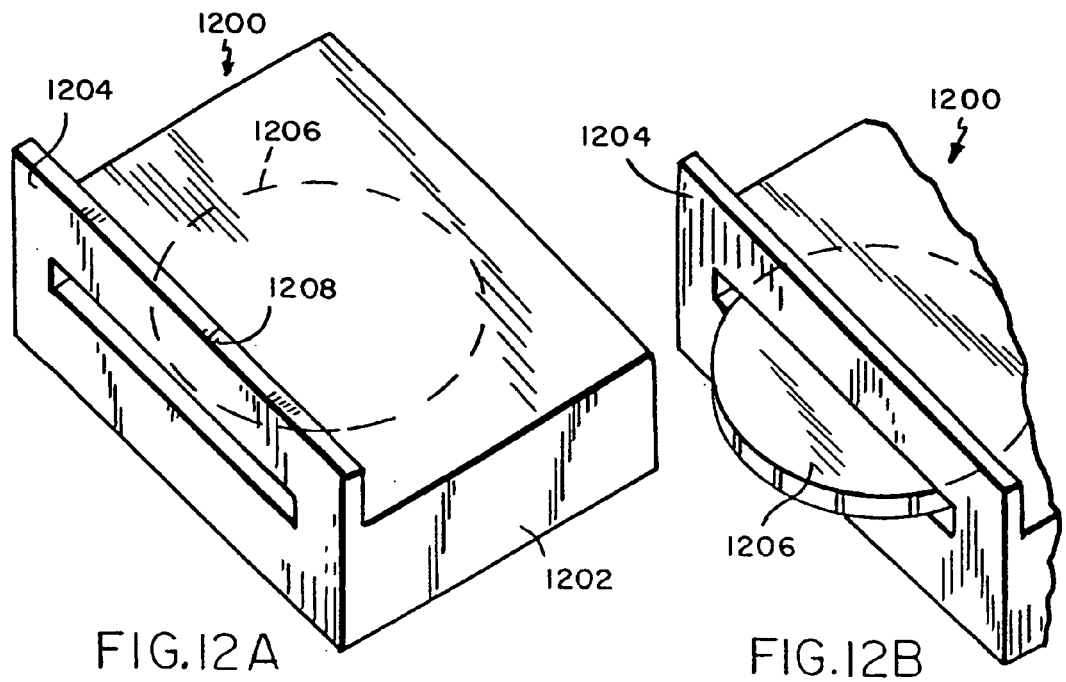
FIG. 12A is a perspective view of a common channel cutting device according to the present invention.
FIG. 12B is a perspective view of a portion of the channel cutting device of FIG. 12A with the cutting implement extended.

In accordance to another method of the present invention, a slot is cut in each of the adjacent vertebral bodies and a biscuit implant is inserted into the slots so as to also bridge across the intervertebral space 4. Preferably the slots are simultaneously cut in the vertebral bodies so a common channel is formed therein. In an exemplary embodiment, and with reference to FIGS. 12A, B there is provided a cutting device 1200 having a cutting implement, for example a circular blade 1206 that is rotated by a motor (not shown). The cutting device 1200 also is configured so the blade 1206 is moveable between a first position, where the blade is disposed within the device housing 1202 (FIG. 12A), and a second position, where a portion of the blade extends outwardly a predetermined distance from an exterior side 1204 of the housing (FIG. 12B). Preferably, the exterior side 1204 from which the blade 1206 extends is configurable so that in one position the exterior side is substantially parallel to a tangent at the midpoint of the blade and further includes indicia 1208 representative of the mid-point of the blade.

Figure 12C:
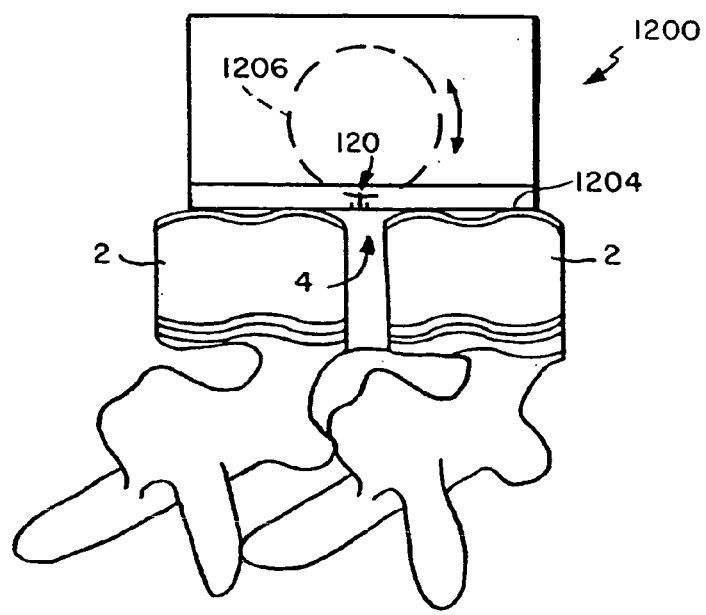
FIG. 12C is a schematic view of the channel cutting device of FIG. 12A disposed on two vertebral bodies.

In use, and as shown in FIG. 12C, the cutting device 1200 is positioned so the device housing exterior side 1204 abuts or is adjacent to the vertebral bodies 2 and so the indicia 1208 representative of the blade midpoint is pointing towards the intervertebral space 4, preferably about a midpoint between the adjacent vertebral bodies. The rotating circular-blade 1206 is then moved from the first to the second position so as to simultaneously cut an arcuate slot in each of the adjacent vertebral bodies 2. After cutting the slot, the circular blade 1206 is returned to the first position with the device housing 1202 and the cutting device 1200 is removed from the vertebral bodies.

Figure 12D:
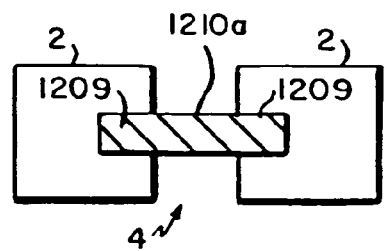
FIG. 12D is a schematic view of the two vertebral bodies to illustrate the implantation of the biscuit implant in the cut common channel.
Figure 12E:
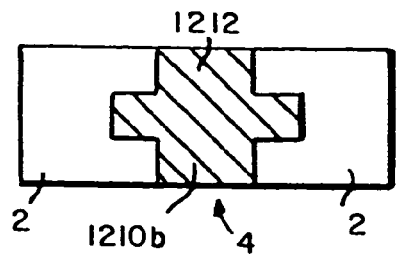
FIG. 12E is another view of the two vertebral bodies to illustrate the implantation of the biscuit implant including a spacing element in the cut common channel.
Figure 12F:
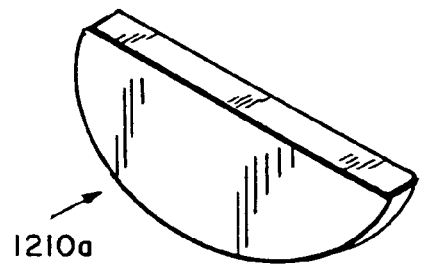
FIG. 12F is a perspective view of the biscuit implant of FIG. 12D.
Figure 12G:
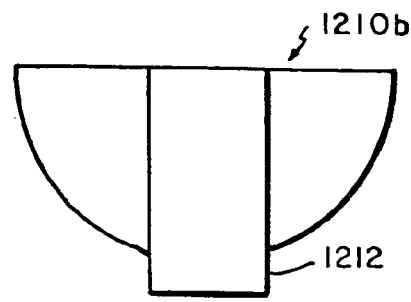
FIG. 12G is a side view of the biscuit implant with spacing element of FIG. 12E.
Figures 12H, 12I, 12J, 12K:
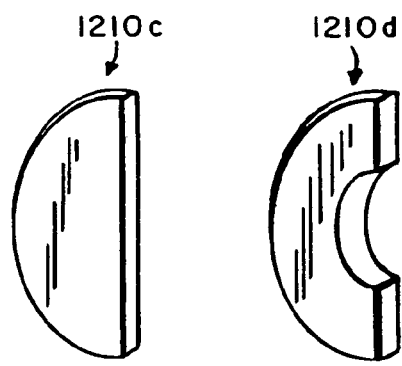
FIGS. 12H–K are perspective views of various exemplary biscuit implants according to the present invention.

As shown in FIG. 12D, after the arcuate slot 1209 is cut in the adjacent vertebrtal bodies 2, a biscuit implant 1210*a* such as that shown in FIG. 12F, is inserted into the arcuate slot in each of the adjacent vertebral bodies and so as to bridge therebetween. The biscuit implant 120*a* is secured in the arcuate slot 1209 using any of the methods described herein for the other implants of the present invention thereby fusing and stabilizing the adjacent vertebral bodies. Alternatively, a biscuit implant 1210*b* such as that shown in FIG. 12G, is configured so as to include a spacer element 1212. Thus, when the biscuit implant 1210*b* is inserted into the arcuate slots 1209 the spacer element 1209 thereof is received and disposed in the intervertebral space 4 as shown in FIG. 12E.

In addition to the exemplary biscuits implants 1210*a,b* illustrated in FIGS. 12F–G, it is within the scope of the present invention for the biscuit implant, whether it is configured with or without a spacer element 1212, to be formed in any of a number of geometric shapes that are otherwise consistent with the intended use. This includes the biscuit implants 1210*c–f* shown in FIGS. 12H–K. Reference shall be made to the foregoing discussion regarding the other implants or fixation members of the present invention as to the materials and other features (e.g., fenestartions) which apply equally for a biscuit implant according to the present invention.

There is shown in FIGS. 13A–13F, an implant system according to these systems and methods. FIG. 13A shows an embodiment of the inner implant 800 adapted for inspection within the outer implant 810 shown in FIG. 13B. The inner implant 800 in FIG. 13A is shown as a substantially hollow device equipped with a fenestrated wall 802. The inner implant 800 bears on a lateral surface 814 a key slat 804 adapted to secure and orient the inner implant 800 within the outer implant 810 shown in FIG. 13B. Specifically, the key slat 804 in the illustrated embodiment can slide into a key groove 808 situated on the inner aspect 818 of the outer implant 810. In the embodiment shown in FIG. 5B, the outer implant is equipped with a trough and trough slit and a fenestrated wall 812 as shown in FIG. 13D. It is understood that the devices shown in these figures can be fabricated from a plurality of materials including both absorbable and non-absorbable biocompatible materials. Materials may include metallics, ceramics, plastics, polymers, biological materials and materials produced by biotechnology. A variety of suitable materials will be readily envisioned by those of ordinary skill in the art for use in the system and methods of the present invention.

FIG. 13C shows a lateral view of two vertebral bodies 820 and 822 showing the general position of the implant system 824. In more detail, the edge of the outer implant 828 is shown imbedded and buried in the vertebral bodies 820 and 822. The edge of the inner implant 830 is shown positioned within the intervertebral disc space 834. A set of bone cuts 832 and 836 are made at the buried end of the implant system 824. FIG. 13D shows an anterior view of the outer implant 838 positioned with the inner implant 840 secured within it according to the systems and methods of the present invention. FIG. 13E shows an anterior view of the inner implant 844 secured within the outer implant 842 according to the systems and methods of the present invention. In FIG. 13E, however, the entire implant system 845 is shown in the rotated 90 degrees relative to the angle at which the implant system 848 is inserted into the vertebral bodies and disc space (not shown). The inner implant 844 in this view assumes a vertical position within the implant system 848, and the outer implant is rotated 90 degrees to effect this repositioning.

FIG. 13F shows in more detail a perspective view of an embodiment of the implant system 850 according to the present invention. The inner implant 854 is shown positioned within the outer implant 858, the entire implant system 850 being turned vertically. As a consequence of this repositioning, two bone sections 860 contained between the inner implant 854 and the outer implant 858 are turned to a vertical position. These bone sections 860 thus provide structural stability to the system 850 and to a spine unit (not shown). The vertical repositioning places cortical bone in a more supportive position.

In the illustrated embodiment, the outer implant 858 is shown with a fenestrated wall 852 for facilitating bony ingrowth. These fenestrations are larger at the upper and lower confines of the repositioned bone graft sites to enhance fusion. Also in the illustratred embodiment, the inner implant 854 is shown with a hollow interior section 862 available for containing a solid displacing shim and bone chips, bone matrices, growth factors or other agents for encouraging or facilitating bony ingrowth and enhancing stable positioning of the verticalized cortical bone sections. Other substances useful to the healing process can be provided within this interior section 862. For example, antibiotics can be placed in this interior section 862 in a suitable vehicle. Other substances and matrices can be envisioned by practitioners of those arts that will fall within the scope of the present invention.

In more specific embodiments, the outer implant 838, 858 is configured so as to include an axially extending slot or slit 841, 864 that is arranged and configured so as to permit adjustment of the diameter of the outer implant, for example to permit the outer implant to be expanded outwardly. Thus, bone sections can be placed with as tight a positioning as possible and the outer implant 838, 858 can be placed in firmer or closer engagement with the vertebral bodies 820, 822. The structure forming the adjustment slit 841, 864 includes any of a number of configurations, structures or arrangements that permit relative movement between the sides of the outer implant on either side of the adjustment slit. Such structures, arrangements and configurations include, but are not limited to an axially extending through aperture or an axially extending ship-lap type of joint where portions of the axially extending sides slidably overlap each other.

Figure 14A:
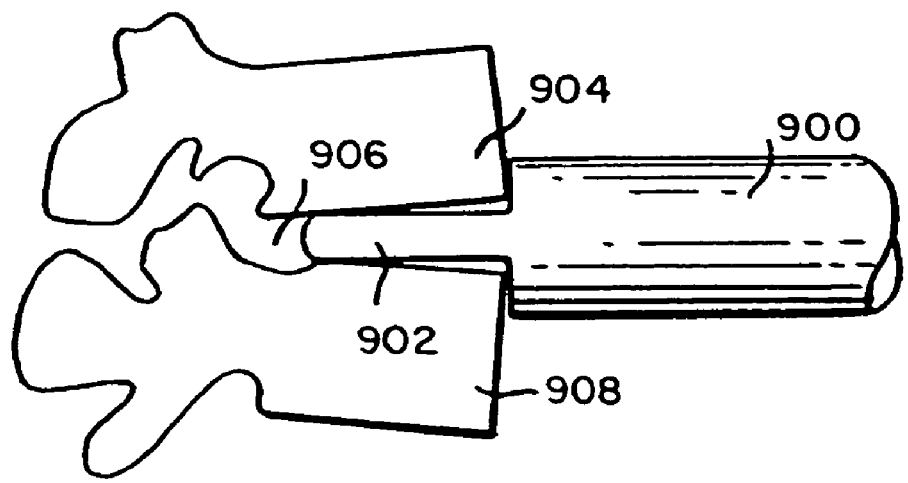
FIG. 14A is a schematic view of an inner tool positioned within the intervertebral disk space.
Figure 14B:
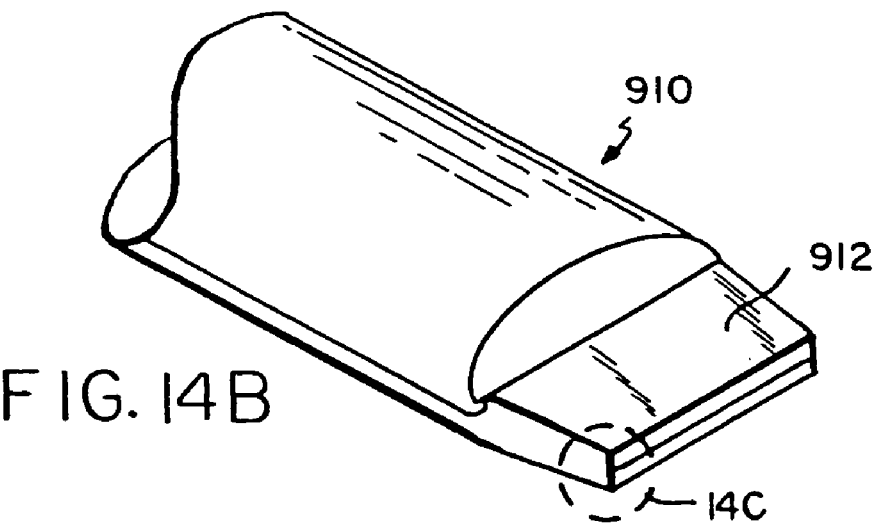
FIG. 14B is an isomeric view of the inner tool.
Figure 14C:
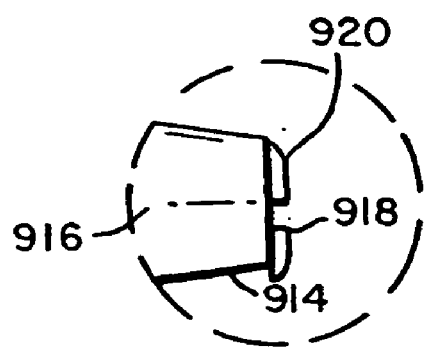
FIG. 14C is a cross-sectional view of the inner tool, with retracted and extended stop-cut blades.

There is generally down in FIGS. 14A–14C, an inner tool 900 to be used according to the systems and methods of the present invention. FIG. 14A shows the inner tool 900 positioned with the intervertebral disc space 906. The inner tool 900 bears on its distal end, a shorter disc end 902 that is adapted for insertion within the intervertebral disc space 906 to allow for cutting a segment of the vertebral bodies 904 and 908 above and below it. FIG. 14B shows a perspective view of an inner tool 910 according to the systems and methods of the present invention. The distal end 912 thereof is adapted for cutting the cortical vertebral end plates that it abuts. FIG. 14C shows in more detail an embodiment of the cutting mechanism bone by the inner tool 916. A cutting end 914 at the distal end of the tool 916 bears a set of stop cut blades shown here in the retracted position 920 and in the extended position 918. Directing the blades from the retracted position 920 to the extended position 918 effects a cut in the adjacent bone (vertebral endplate, not shown). While the depicted embodiment of a tool can be advantageously employed in conjunction with the implant system according to these systems and methods other tools and devices can be envisioned by skilled practitioners of these arts for cutting bone and for positioning an implant system all modification that fall within the scope of the present invention.

Figure 15:
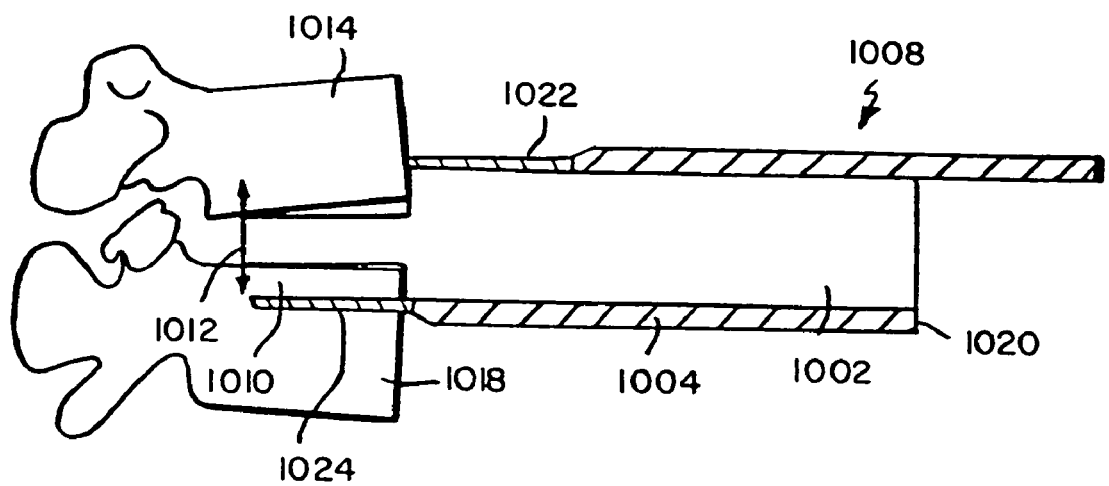
FIG. 15 is a schematic view of the inner and outer tool system positioned in relation to the vertebral bodies.

FIG. 15 shows a lateral view of an embodiment of the tool system 1000 according to the present invention positioned in relation to the vertebral bodies 1014 and 1018. In this view an inner tool 1002 is shown with its distal end positioned between the vertebral bodies 1014 and 1018. An outer tool 1004 is shown in two positions, a position 1008 before driving it into the vertebral bodies 1014 and 1018 and a position 1020 after driving it into the vertebral bodies 1014 and 1018. A blade 1022 of the outer tool 1004 is shown positioned at the anterior aspect of the vertebral body 1014 before the outer tool 1004 is driven into the vertebral body 1014. In this position 1020 after driving the tool 1004 into the vertebral body 1018, the blade 1024 is shown imbedded in the vertebral body 1018, having cut it perpendicular to its anterior face. The inner tool 1002 can make bone cuts 1012 at right angles to the blade 1024 of the outer tool 1004, thereby creating a bone slab 1010 that can be repositioned according to the systems and methods of the present invention. This bone slab 1010 (section) can be cut so as to allow for anterior vertebral distraction by making these slabs oblong rather than circular.

Figure 16:
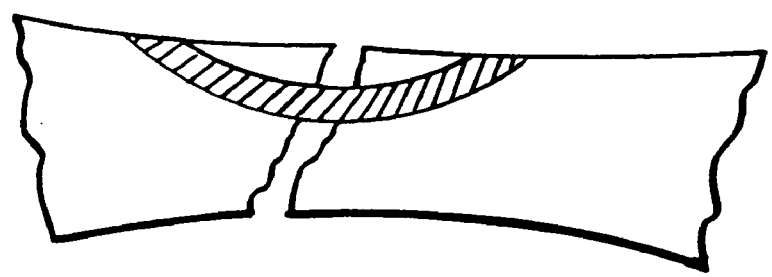
FIG. 16 is a schematic view showing bone-to-bone with no gap application.

It should be clear that the methods, systems, and devices of the invention are not limited to securing a pair of vertebrae, but rather any combination of multiple vertebrae segments. It also should be clear that the methods, systems, and devices are in no way limited to vertebrae segments. In particular, the invention enables securing any solid substrates, particularly bone substrates, without use of protruding screws or plates. In this regard, FIG. 16 shows a bone-to-bone application using techniques of the invention. It also should be understood that the invention is applicable to a wide variety of fixation configurations, including bone-to-bone with a gap; bone-to-bone without a gap; bone-tobone with bony spacers; and bone-to-bone with a non-bony spacer such as a metal, polymer, or a biodegradable material.

Although a preferred embodiment of the invention has been described using specific terms, such description is for illustrative purposes only, and it is to be understood that changes and variations may be made without departing from the spirit or scope of the following claims.

What is claimed is:

1. A spinal intravertebral prosthetic system, comprising:
   an intravertebral prosthetic device;
   an arcuate implant member of a size sufficient to extend between two adjacent vertebrate;
   wherein the intravertebral prosthetic device is configured to receive therein a portion of the arcuate implant member; and
   wherein the portion of the arcuate implant member that passes through the intravertebral prosthetic device is made from a compressible material.

2. The spinal intravertebral prosthetic system of claim 1 wherein the compressible material is one of silicon, elastomeric polymers, polyurethances and copolymers thereof, hydrogels, collagen, bioabsorbables, compositions, a metallic spring or coil, or a material that allows continual mobility between the vertebral bodies.

3. The spinal intravertebral prosthetic system of claim 2 wherein the intravertebral prosthetic device comprises a compressible material.

4. The spinal intravertebral prosthetic system of claim 3 wherein the compressible material is one of silicon, elastomeric polymers, polyurethanes and copolymers thereof, hydrogels, collagen or bioabsorbables.

5. The spinal intravertebral prosthetic system of claim 1, wherein the implant includes a non-flexible portion made of a material conducive to attachment to the vertebrae.

6. The spinal intravertebral prosthetic system of claim 5, wherein the non-flexible portion of the implant is made from one or more of a metal, bone, morphogenic protein, carbon fiber composite, nitinol, a biodegradable material, collagen or collagen coated metal or bone.

7. The spinal intravertebral prosthetic system of claim 1, wherein the compressible portion of the implant is disposed between end sections, each end section being made of non-flexible material conducive to attachment to the vertebrae.

8. The spinal intravertebral prosthetic system of claim 7, wherein the non-flexible material is made from one or more of a metal, bone, morphogenic protein, carbon fiber composite, nitinol, a biodegradable material, collagen or collagen coated metal or bone.

9. A spinal intravertebral prosthetic device kit comprising:
   an intravertebral prosthetic device;
   an arcuate fixation member;
   wherein the intravertebral prosthetic device is configured to receive therein a portion of the arcuate fixation member; and
   wherein the portion of the fixation member that passes through the intravertebral prosthetic device, is made from a compressible material.

10. The implantable spinal intravertebral prosthetic device kit of claim 9, wherein the arcuate fixation member is configured to also extend through a preformed aperture in each of the two adjacent vertebrae.

11. A spinal intravertebral prosthetic device kit comprising:
    a positioning apparatus including:
    two guide sleeves, each guide sleeve having a long axis,
    a cross member,
    an intravertebral spacer,
    wherein the guide sleeves are pivotably mounted to the cross member, and
    wherein the intravertebral spacer is spaced from the cross member and interconnected thereto so as to be between the pivots points for the guide sleeves;
    an intravertebral prosthetic device;
    a fixation member; and
    wherein a portion of the fixation member, passing through the intravertebral prosthetic device is made from a compressible material.

12. The spinal intravertebral prosthetic device kit of claim 11 wherein the compressible material is one of silicon, elastomeric polymers, polyurethances and copolymers thereof, hydrogels, collagen, bioabsorbables, compositions, a metallic spring or coil, or a material that allows continual mobility between the vertebral bodies.

13. The spinal intravertebral prosthetic device kit of claim 12 wherein the intravertebral prosthetic device comprises a compressible material.

14. The spinal intravertebral prosthetic device kit of claim 13 wherein the compressible material is one of silicon, elastomeric polymers, polyurethanes and copolymers thereof, hydrogels, collagen or bioabsorbables.

15. The spinal intravertebral prosthetic device kit of claim 11, wherein the fixation member includes a non-flexible portion made of a material conducive to attachment to the vertebrae.

16. The spinal intravertebral prosthetic device kit of claim 15, wherein the non-flexible portion is made from one or more of a metal, bone, morphogenic protein, carbon fiber composite, nitinol, a biodegradable material, collogen or collagen coated metal or bone.

17. The spinal intravertebral prosthetic device kit of claim 11, wherein the compressible portion of the fixation member is disposed between end sections, each end section being made of non-flexible material conducive to attachment to the vertebrae.

18. The spinal intravertebral prosthetic device kit of claim 17, wherein the non-flexible material is one or more of a metal, bone, morphogenic protein, carbon fiber composite, nitinol, a biodegradable material, collagen or collagen coated metal or bone.

19. The spinal intravertebral prosthetic device kit of claim 11, wherein the fixation member is arcuate.

20. A spinal system comprising:
    an arcuate member and an intravertebral prosthetic device that are capable of being surgically implanted in a mammalian spine;
    wherein the arcuate member extends between two adjacent vertebrae when implanted,
    wherein the intravertebral prosthetic device is configured to receive therein a portion of the arcuate implant member;
    wherein the arcuate member is configured so as to extend through a preformed aperture in each of the two adjacent vertebrae; and
    wherein the portion of the arcuate implant member that passes through the intravertebral prosthetic device is made from a compressible material.

21. The spinal system of claim 20, wherein the intravertebral prosthetic device comprises a compressible material.

22. An implantable spinal intravertebral prosthetic system, comprising:
    an intravertebral prosthetic device;
    an arcuate implant member of a size sufficient to extend between two adjacent vertebrae;

wherein the intravertebral prosthetic device is configured to receive therein a portion of the arcuate implant member;

wherein the implant member is sized so as to extend through a pre-formed aperture in each of the two adjacent vertebrae; and wherein the arcuate implant member is configured so as to have a uniform outer diameter.

23. The implantable spinal intravertebral prosthetic system of claim 22, wherein the preformed aperture in each of the adjacent vertebrae is of a constant radius and wherein the arcuate implant member is configured so as to extend through each constant radius preformed aperture.

24. The implantable spinal intravertebral prosthetic system of claim 22, wherein the arcuate implant member is configured so as to be secured by fixation points within the adjacent vertebrae.

25. The implantable spinal intravertebral prosthetic system of claim 22, wherein the arcuate implant member is configured and sized so as to be a load bearing member.

26. An implantable spinal intravertebral prosthetic system, comprising:

an intravertebral prosthetic device;

an arcuate implant member of a size sufficient to extend between two adjacent vertebrae;

wherein the intravertebral prosthetic device is configured to receive therein a portion of the arcuate implant member;

wherein the implant member is sized so as to extend through a pre-formed aperture in each of the two adjacent vertebrae; and a plurality of securing mechanisms one for each of the adjacent vertebrae, each securing mechanism being configured so as to secure the securing mechanism to one of the adjacent vertebrae, wherein the arcuate implant member is configured so as to be secured to each of the adjacent vertebrae by the plurality of securing mechanisms.

27. The implantable spinal intravertebral prosthetic system of claim 26, wherein each end portion of the arcuate implant member is configured so as to be secured respectively to one of the adjacent vertebrae by one of the plurality of securing mechanisms, thereby further securing the arcuate implant member to the adjacent vertebrae.

28. An implantable spinal intravertebral prosthetic system, comprising:

an intravertebral prosthetic device;

an arcuate implant member of a size sufficient to extend between two adjacent vertebrate vertebrae;

wherein the intravertebral prosthetic device is configured to receive therein a portion of the arcuate implant member;

wherein the implant member is sized so as to extend through a pre-formed aperture in each of the two adjacent vertebrae; and wherein the portion of the arcuate implant member that is received in the intravertebral prosthetic device, is made from a compressible material.

29. The implantable spinal intravertebral prosthetic system of claim 28 wherein the intravertebral prosthetic device comprises a compressible material.

30. An implantable spinal intravertebral prosthetic system, comprising:

an intravertebral prosthetic device;

an arcuate implant member of a size sufficient to extend between two adjacent vertebrate;

a plurality of securing mechanisms one for each of the adjacent vertebrae, each securing mechanism being configured so as to secure the securing mechanism to one of the adjacent vertebrae;

wherein the intravertebral prosthetic device is configured to receive therein a portion of the arcuate implant member; and wherein each of the plurality of securing mechanisms is configured so as to mechanically engage separate portions of the arcuate implant member, thereby securing the arcuate implant member to each of the adjacent vertebrae.

31. The implantable spinal intravertebral prosthetic system of claim 30, wherein the arcuate implant member is sized so as to extend through a pre-formed aperture in each of the two adjacent vertebrae.

32. The implantable spinal intravertebral prosthetic system of claim 30, wherein each of the plurality of securing mechanisms are configured so as to be threadably secured respectively in one of the adjacent vertebrae.

33. The implantable spinal intravertebral prosthetic system of claim 30, wherein the portion of the arcuate implant member that passes through the intravertebral prosthetic device, is made from a compressible material.

34. The implantable spinal intravertebral prosthetic system of claim 33 wherein the intravertebral prosthetic device comprises a compressible material.

35. A method for securing an intravertebral prosthetic device between vertebrae, comprising the steps of:

implanting an arcuate fixation member between the vertebrae, where each end of the fixation member is secured to one of the vertebrae; and passing a portion of the arcuate fixation member through the intravertebral prosthetic device, wherein at least the portion of the fixation member that is passing through the intravertebral prosthetic device is made from a compressible material.

36. A method for securing an intravertebral prosthetic device between adjacent vertebrae, comprising:

implanting an arcuate fixation member between the vertebrae;

passing a portion of the arcuate fixation member through the intravertebral prosthetic device;

wherein a portion of the fixation member is made from a compressible material; and wherein the fixation member is implanted through a preformed aperture in each of the adjacent vertebrae.

37. The method of claim 36 wherein the pre-formed aperture in one of the adjacent vertebrae is a partially pre-formed aperture.

38. The method of claim 36 wherein the preformed aperture has been drilled in each of the adjacent vertebrae.

39. The method of claim 36 wherein the fixation member is the sole apparatus employed to maintain the location and orientation of the intravertebral prosthetic device.

40. The method of claim 36 wherein the compressible material is one of silicon, elastomeric polymers, polyurethances and copolymers thereof, hydrogels, collagen, bioabsorbables, compositions, a metallic spring or coil, or a material that allows continual mobility between the vertebral bodies.

41. The method of claim 40 wherein the intravertebral prosthetic device comprises a compressible material.

42. The method of claim 41 wherein the compressible material is one of silicon, elastomeric polymers, polyurethances and copolymers thereof, hydrogels, collagen or bioabsorbables.

43. The method of claim 36, wherein the fixation member includes a non-flexible portion made of a material conducive to attachment to the vertebrae.

44. The method of claim 43, wherein the non-flexible portion of the fixation member is made from one or more of a metal, bone, morphogenic protein, carbon fiber composite, nitinol, a biodegradable material, collagen or collagen coated metal or bone.

45. The method of claim 36, wherein the compressible portion of the fixation member is disposed between end sections, each end section being made of non-flexible material conducive to attachment to the vertebrae.

46. The method of claim 45, wherein the non-flexible material is made from one or more of a metal, bone, morphogenic protein, carbon fiber composite, nitinol, a biodegradable material, collagen or collagen coated metal or bone.

47. The method of claim 36 wherein the fixation member is one of solid, hollow or with ingrowth fenestrations and screw holes or expansion bolts or staples.

48. A method for securing an intravertebral prosthetic device of a spine, comprising:
providing a positioning apparatus including two guide sleeves, each guide sleeve having a long axis;
locating the two guide sleeves with respect to the adjacent vertebrae such that a vertex formed by the long axis of each guide sleeve is located in the intervertebral space of the adjacent vertebrae;
forming an aperture in each of the adjacent vertebrae using at least one of the guide sleeves;
inserting an implant into the apertures formed in each of the adjacent vertebrae so that the implant extends between the adjacent vertebrae and through the intervertebral space and so a portion of the implant passes through the intravertebral prosthetic device, wherein the portion of the implant is made from a compressible material.

49. The method of claim 48 wherein said step of forming includes forming an arcuate aperture in each of the adjacent vertebrae such that the arcuate apertures in the adjacent vertebrae have a common axis of rotation.

50. The method of claim 48 wherein the implant is inserted through a through aperture in one of the adjacent vertebrae and in a partially formed aperture in the other of the adjacent vertebrae.

51. The method of claim 48 wherein the implant is the sole apparatus employed to maintain the location and orientation of the intravertebral prosthetic device.

52. The method of claim 48 wherein the compressible material is one of silicon, elastomeric polymers, polyurethances and copolymers thereof, hydrogels, collagen, bioabsorbables, compositions, a metallic spring or coil, or a material that allows continual mobility between the vertebral bodies.

53. The method of claim 52 wherein the intravertebral prosthetic device comprises a compressible material.

54. The method of claim 53 wherein the compressible material is one of silicon, elastomeric polymers, polyurethanes and copolymers thereof, hydrogels, collagen or bioabsorbables.

55. The method of claim 48, wherein the implant includes a non-flexible portion made of a material conducive to attachment to the vertebrae.

56. The method of claim 55, wherein the non-flexible portion of the implant is made from one or more of a metal, bone, morphogenic protein, carbon fiber composite, nitinol, a biodegradable material, collagen or collagen coated metal or bone.

57. The method of claim 48, wherein the compressible portion of the implant is disposed between end sections, each end section being made of non-flexible material conducive to attachment to the vertebrae.

58. The method of claim 57, wherein the non-flexible material is made from one or more of a metal, bone, morphogenic protein, carbon fiber composite, nitinol, a biodegradable material, collagen or collagen coated metal or bone.

59. The method of claim 48 wherein the step of inserting includes:
inserting a beginning end of the implant into an entrance opening of one of the adjacent vertebrae;
applying a force to the portion of the implant extending from the entrance opening so as to drive the implant beginning end though the aperture in the aperture of said one of the adjacent vertebrae, through the intervertebral space and into the aperture in the other of the adjacent vertebrae.

60. A method for securing an intravertebral prosthetic device, comprising:
providing a positioning apparatus including a pivot arm that is rotatable about a pivot point;
locating the positioning apparatus with respect to the adjacent vertebrae such that the pivot point is disposed between the adjacent vertebrae;
forming an aperture in each of the adjacent vertebrae responsive to rotation of the pivot arm about the pivot point, one of the apertures being formed is a through aperture; and
inserting an implant into the apertures formed in each of the adjacent vertebrae so that the implant extends between the adjacent vertebrae and through the intervertebral space and passes through a portion of the intravertebral prosthetic device, wherein a portion of the fixation member is made from a compressible material.

61. The method of claim 60 wherein said aperture in each of the adjacent vertebrae is arcuate.

62. The method of claim 60 wherein the compressible material is one of silicon, elastomeric polymers, polyurethances and copolymers thereof, hydrogels, collagen, bioabsorbables, compositions, a metallic spring or coil, or a material that allows continual mobility between the vertebral bodies.

63. The method of claim 62 wherein the intravertebral prosthetic device comprises a compressible material.

64. The method of claim 63 wherein the compressible material is one of silicon, elastomeric polymers, polyurethanes and copolymers thereof, hydrogels, collagen or bioabsorbables.

65. The method of claim 60, wherein the implant includes a non-flexible portion made of a material conducive to attachment to the vertebrae.

66. The method of claim 65, wherein the non-flexible portion of the implant is made from one or more of a metal, bone, morphogenic protein, carbon fiber composite, nitinol, a biodegradable material, collagen or collagen coated metal or bone.

67. The method of claim 60, wherein the compressible portion of the implant is disposed between end sections, each end section being made of non-flexible material conducive to attachment to the vertebrae.

68. The method of claim 67, wherein the non-flexible material is made from one or more of a metal, bone, morphogenic protein, carbon fiber composite, nitinol, a biodegradable material, collagen or collagen coated metal or bone.

69. The method of claim 60, wherein the step of forming includes forming by one of drilling or ablation of the bone by an energy source.

70. The stabilizing method of claim 60 wherein the apparatus being provided further includes a drill that is affixed to the pivot arm such that when the pivot arm rotates about the pivot point the drill follows a defined arcuate cutting path.

71. The method of claim 70 wherein the drill includes a curved drilling element.

72. The method of claim 71 wherein the curved drilling element comprises a curved cannula, a flexible member disposed within the curved cannula, and a cutting burr affixed to an end of the flexible member, the flexible burr for cutting an arcuate aperture in each of the adjacent vertebrae.

73. The method of claim 70 wherein the step of forming includes rotating the pivot arm so that a through aperture is formed in one of the adjacent vertebrae and so a partially formed aperture is formed in the other of the adjacent vertebrae.

74. The method of claim 70 wherein the step of forming includes rotating the pivot arm so that a through aperture is formed in each of the adjacent vertebrae.

75. A method for locating compressible material in an intravertebral space between vertebral endplates of a spine, said method comprising the steps of:
  creating an arcuate preformed aperture in a vertebral body that extends through the vertebral endplate of the spine;
  placing compressible material though the preformed aperture such that the compressible material is disposed between the vertebral endplates; and
  filling at least a portion of the preformed aperture with an arcuate member of a non-compressible material.

* * * * *